(12) United States Patent
Hayashi

(10) Patent No.: US 8,646,913 B2
(45) Date of Patent: Feb. 11, 2014

(54) OPTICAL IMAGE MEASURING DEVICE AND CONTROL METHOD THEREOF

(75) Inventor: Takefumi Hayashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 190 days.

(21) Appl. No.: 13/142,938

(22) PCT Filed: Dec. 7, 2009

(86) PCT No.: PCT/JP2009/006672
§ 371 (c)(1),
(2), (4) Date: Jun. 30, 2011

(87) PCT Pub. No.: WO2010/079550
PCT Pub. Date: Jul. 15, 2010

(65) Prior Publication Data
US 2011/0267583 A1 Nov. 3, 2011

(30) Foreign Application Priority Data

Jan. 6, 2009 (JP) ................................. 2009-000529

(51) Int. Cl.
*A61B 3/14* (2006.01)
*A61B 3/00* (2006.01)

(52) U.S. Cl.
CPC ...................... *A61B 3/14* (2013.01)
USPC ............................ 351/206; 351/208; 351/246

(58) Field of Classification Search
USPC .................................. 351/205, 206, 208, 246
See application file for complete search history.

(56) References Cited

U.S. PATENT DOCUMENTS

| 6,377,349 | B1 | 4/2002 | Fercher |
| 7,345,770 | B2 | 3/2008 | Chan et al. |
| 2007/0002277 | A1 | 1/2007 | Hanebuchi |
| 2008/0285043 | A1 | 11/2008 | Fercher et al. |

FOREIGN PATENT DOCUMENTS

| JP | 09-276232 A | 10/1997 |
| JP | 10-267610 A | 10/1998 |
| JP | 11-325849 A | 11/1999 |
| JP | 2002-139421 A | 5/2002 |
| JP | 2006-153838 A | 6/2006 |
| JP | 2007-024677 A | 2/2007 |
| JP | 2007-037984 A | 2/2007 |
| JP | 2008-073099 A | 4/2008 |
| JP | 2008-272256 A | 11/2008 |
| WO | 2007/065670 A2 | 6/2007 |

OTHER PUBLICATIONS

International Search Report for PCT/JP2009/006672 dated Jan. 19, 2010.

*Primary Examiner* — Jack Dinh
(74) *Attorney, Agent, or Firm* — Pearne & Gordon LLP

(57) ABSTRACT

A low-coherence light is split into a signal light and a reference light. The optical path length of the reference light is switched to optical path lengths that correspond to a first depth zone and a second depth zone. When forming a tomographic image of the second depth zone, in an optical system that condenses the signal light to the first depth zone when a measured object and an objective lens are located at a predetermined working distance, while being positioned at the working distance, a depth zone switching lens that transitions the depth at which the signal light is condensed to the second depth zone is inserted.

11 Claims, 19 Drawing Sheets

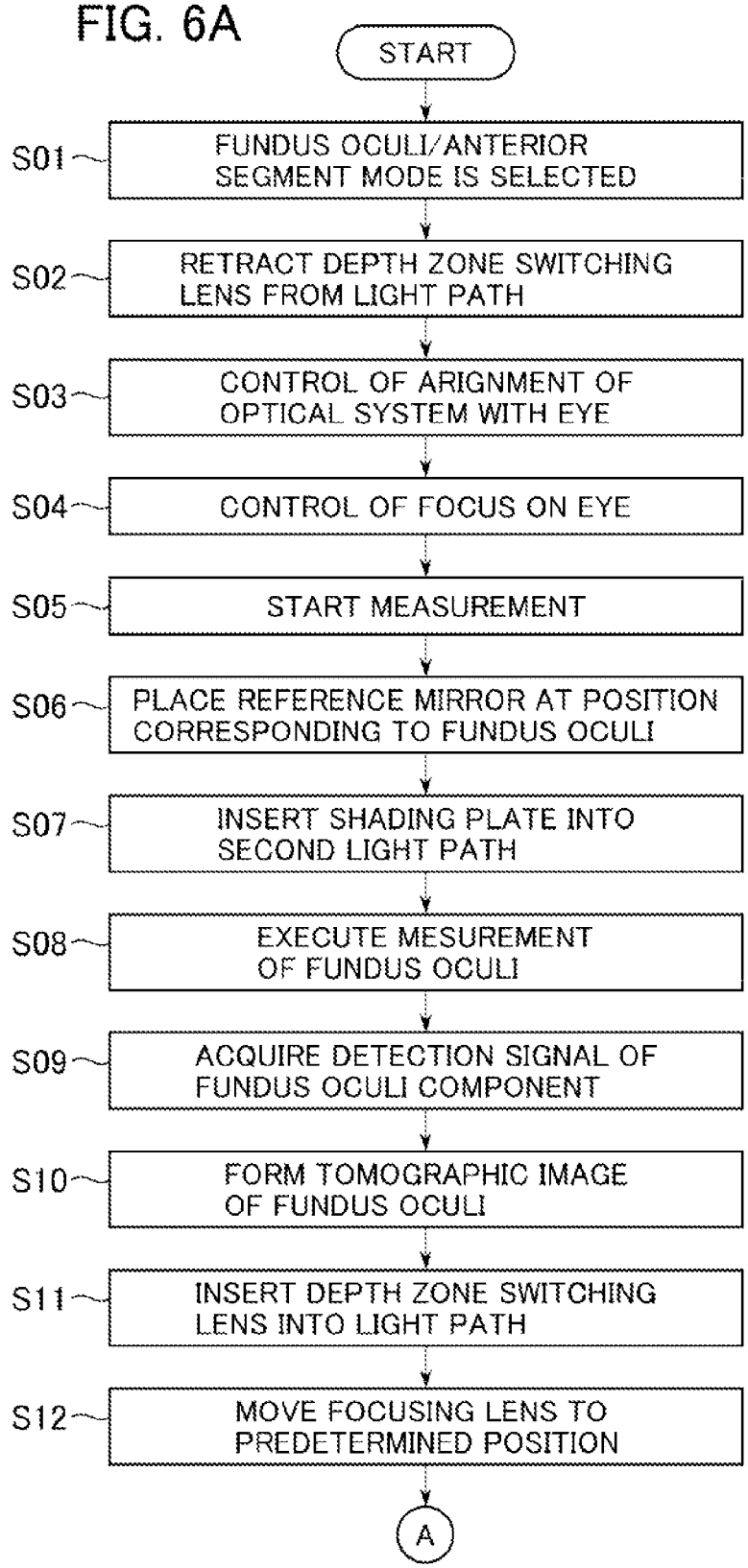

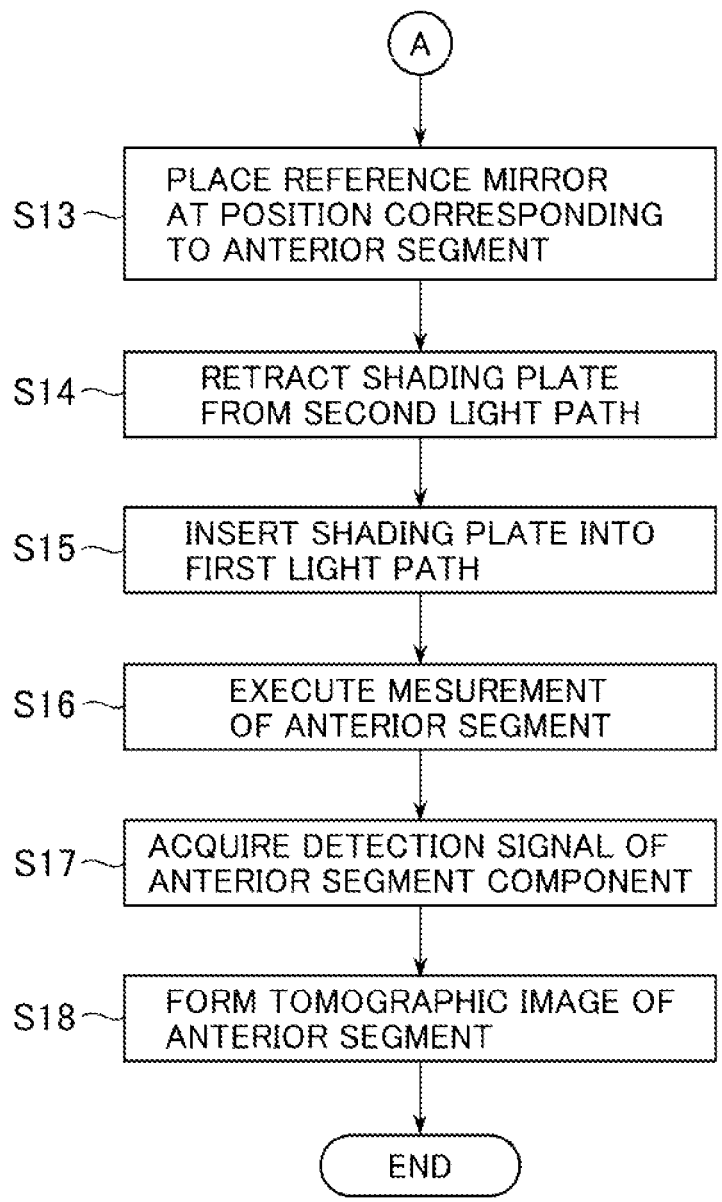

OPTICAL IMAGE MEASURING DEVICE AND CONTROL METHOD THEREOF

TECHNICAL FIELD

The present invention relates to an optical image measuring device configured to form images that show the surface morphology and internal morphology of measured objects by using a light beam, and a control method thereof.

BACKGROUND ART

In recent years, an optical image measuring technique of forming images that show the surface morphology and internal morphology of measured objects by using a light beam from a laser light source or the like has attracted attention. Unlike an X-ray CT apparatus, the optical image measuring technique is noninvasive to human bodies, and is therefore expected to be utilized more particularly in the medical field and biological field.

Japanese Unexamined Patent Application Publication No. Hei 11-325849 (Patent Document 1) discloses a device to which the optical image measuring technique is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of the Patent Document 1 uses a technique of so-called "Fourier Domain OCT (Optical Coherence Tomography)." That is to say, the device radiates a low-coherence light beam to a measured object, superposes the reflected light and the reference light to generate an interference light, and acquires the spectral intensity distribution of the interference light to execute Fourier transform, thereby imaging the morphology in the depth direction (the z-direction) of the measured object.

Furthermore, the device described in the Patent Document 1 is provided with a Galvano mirror that scans with a light beam (a signal light), and is thereby configured to form an image of a desired measurement target region of the measured object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Japanese Unexamined Patent Application Publication No. 2002-139421 (Patent Document 2) discloses a technique of scanning with a signal light in the horizontal direction and the vertical direction to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Japanese Unexamined Patent Application Publication No. 2007-24677 (Patent Document 3) and Japanese Unexamined Patent Application Publication No. 2006-153838 (Patent Document 4) disclose other types of optical image measuring devices. The Patent Document 3 describes an optical image measuring device that images the morphology of a measured object by scanning the measured object with light of various wavelengths, acquiring the spectral intensity distribution based on an interference light obtained by superposing the reflected lights of the light of the respective wavelengths on the reference light, and executing Fourier transform. Such an optical image measuring device is called a Swept Source type or the like.

Further, the Patent Document 4 describes an optical image measuring device that radiates a light having a predetermined beam diameter to a measured object and analyzes the components of an interference light obtained by superposing the reflected light and the reference light, thereby forming an image of the measured object in a cross-section orthogonal to the travelling direction of the light. Such an optical image measuring device is called a full-field type, en-face type or the like.

Japanese Unexamined Patent Application Publication No. 2008-73099 (Patent Document 5) discloses a configuration in which the OCT technique is applied to the ophthalmologic field. Before the optical image measuring device was applied to the ophthalmologic field, a fundus oculi observing device such as a retinal camera had been used (for example, refer to Japanese Unexamined Patent Application Publication No. Hei 09-276232 (Patent Document 6)).

A fundus oculi imaging device using the OCT technique has a merit that a tomographic image and three-dimensional image of the fundus oculi can be acquired, as compared with a retinal camera that merely images the fundus oculi surface from the front. Therefore, contribution to increase of the diagnosis accuracy and early detection of a lesion is expected. Moreover, the application field of an optical image measuring device using this OCT technique has been extended to measurement use of various physical quantities of eyes such as the ocular axial length, the size of a lesion site and a chamber angle.

Consequently, in Japanese Unexamined Patent Application Publication No. 2007-37984 (Patent Document 7), an optical image measuring device that measures the axial length from the corneal reflection light and the fundus oculi reflection light and obtains OCT images of the anterior segment based on the reflection light of a signal light from the cornea and the reference light, or an optical image measuring device that measures the axial length from the corneal reflection light and the fundus oculi reflection light and obtains OCT images of the fundus oculi based on the reflection light of the signal light from the fundus oculi and the reference light are disclosed. That is, a technology that can measure axial lengths and obtain OCT images of the anterior segment or the fundus oculi with a single device is disclosed.

As described above, obtaining a variety of organism information of an eye with a single device is desired from the viewpoint of examination efficiency and particularly in recent years, a technology that can obtain both OCT images of the fundus oculis and anterior segments with a single optical image measuring device is anticipated.

However, with the optical image measuring device, when attempting to obtain a vivid tomographic image, a signal light is required to be efficiently focused on the depth zone of its image target. Generally, in the imaging optical system through which the signal light passes, the position on which the signal light is focused is fixed to one region and focus is blurred in other regions.

FIG. 13 is a diagram that shows part of a common imaging optical system. A signal light that exits from an end face 152b of an optical fiber 152a enters into a lens 142 and becomes a parallel light flux. This signal light that became the parallel light flux is then condensed to one region via a scan unit 141 that has a galvanometer mirror, etc., an imaging lens 126, a relay lens 125, a focusing lens 124, and an objective lens 113. When a working distance Wd such that the signal light condenses on a fundus oculi Ef of an eye E is matched with the distance between the objective lens 113 and a corneal vertex Ec, the anterior segment Ea is not focused.

Therefore, although a variety of organism information can be obtained as a vivid tomographic image from OCT images of the fundus oculi Ef shown in FIG. 14B, according to OCT images of the anterior segment Ea shown in FIG. 14A, because the corneal reflection light from the vertex Ec is of high intensity, it can be distinguished, but because distinguishing the other part such as a posterior surface of the cornea or crystalline lens is difficult, this organism information is almost impossible to obtain.

Consequently, for example, a photographing method in which after matching the working distance Wd such that the signal light is focused on the fundus oculi Ef of the eye E to the distance between the objective lens 113 and the corneal vertex Ec, an OCT image of the fundus oculi Ef is first obtained, then an OCT image of the anterior segment Ea is obtained after changing the distance between the objective lens 113 and the corneal vertex Ec to the working distance Wd such that the signal light is focused on the anterior segment Ea of the eye E, can be considered.

However, with this photographing method, because a total of two adjustments of the distance between the objective lens 113 and the corneal vertex Ec must be performed, the examination time becomes long and both the examiners and subject bear a large burden.

Patent Document 1: Japanese Unexamined Patent Application Publication No. Hei 11-325849
Patent Document 2: Japanese Unexamined Patent Application Publication No. 2002-139421
Patent Document 3: Japanese Unexamined Patent Application Publication No. 2007-24677
Patent Document 4: Japanese Unexamined Patent Application Publication No. 2006-153838
Patent Document 5: Japanese Unexamined Patent Application Publication No. 2008-73099
Patent Document 6: Japanese Unexamined Patent Application Publication No. Hei 09-276232
Patent Document 7: Japanese Unexamined Patent Application Publication No. 2007-37984

DISCLOSURE OF THE INVENTION

Problem that the Invention is to Solve

The present invention is made for solving the abovementioned problems, and an object of the present invention is to provide an optical image measuring device which can obtain vivid OCT images of a plurality of depth zones with a single device and shorten its measurement time, and control method thereof.

Means for Solving the Problem

In order to achieve the above object, the present invention is an optical image measuring device that forms tomographic images of at least a first depth zone and a second depth zone of a measured object, respectively, comprising: a splitting part configured to split a light from a light source into a signal light and a reference light; a first light path configured to be capable of adjusting an optical path length of said reference light to an optical path length that corresponds to said first depth zone; a second light path configured to be capable of adjusting an optical path length of said reference light to an optical path length that corresponds to said second depth zone; an optical system comprising an objective lens and a focusing lens, and configured to illuminate said measured object with said signal light; an optical system comprising an objective lens and a focusing lens, and configured to condense said signal light into said first depth zone; an interference light generation part configured to generate an interference light by causing interference with said signal light reflected from said first depth zone and said reference light via said first light path and generate an interference light by causing interference with said signal light reflected from said second depth zone and said reference light via said second light path; a detecting part configured to detect each of the interference light corresponding to said first depth zone and the interference light corresponding to said second depth zone; and an image forming part configured to form tomographic images of said first depth zone and said second depth zone, respectively, based on the detection by said detecting part.

Effect of the Invention

According to the present invention, even if an optical system that can condense a signal light to the first depth zone is obtained, by inserting a depth zone switching lens and switching light path of the reference light to an optical path length that corresponds to a second depth zone by a switching part, the signal light reflected by the second depth zone that is different from the first depth zone can be efficiently collected. Therefore, even with an optical image measuring device that has an optical system that mainly measures the first depth zone, detailed information of each depth position of the second depth zone can be collected and this entire second depth zone can be vividly photographed.

For example, when the first depth zone is considered to be a fundus oculi and the second depth zone is considered to be an anterior segment, this optical image measuring device can obtain not only vivid OCT images of the fundus oculi but also vivid OCT images of the anterior segment by inserting the depth zone switching lens. In OCT images of the anterior segment that are obtained by this optical image measuring device, not only the surface of a cornea but also each layer position of an anterior segment is vividly shown.

BRIEF DESCRIPTION OF THE DRAWINGS

FIG. 6A is a flow chart showing the first half of the first operation of the optical image measuring device according to the present embodiment.

FIG. 6B is a flow chart showing the second half of the first operation of the optical image measuring device according to the present embodiment.

Figure 1:
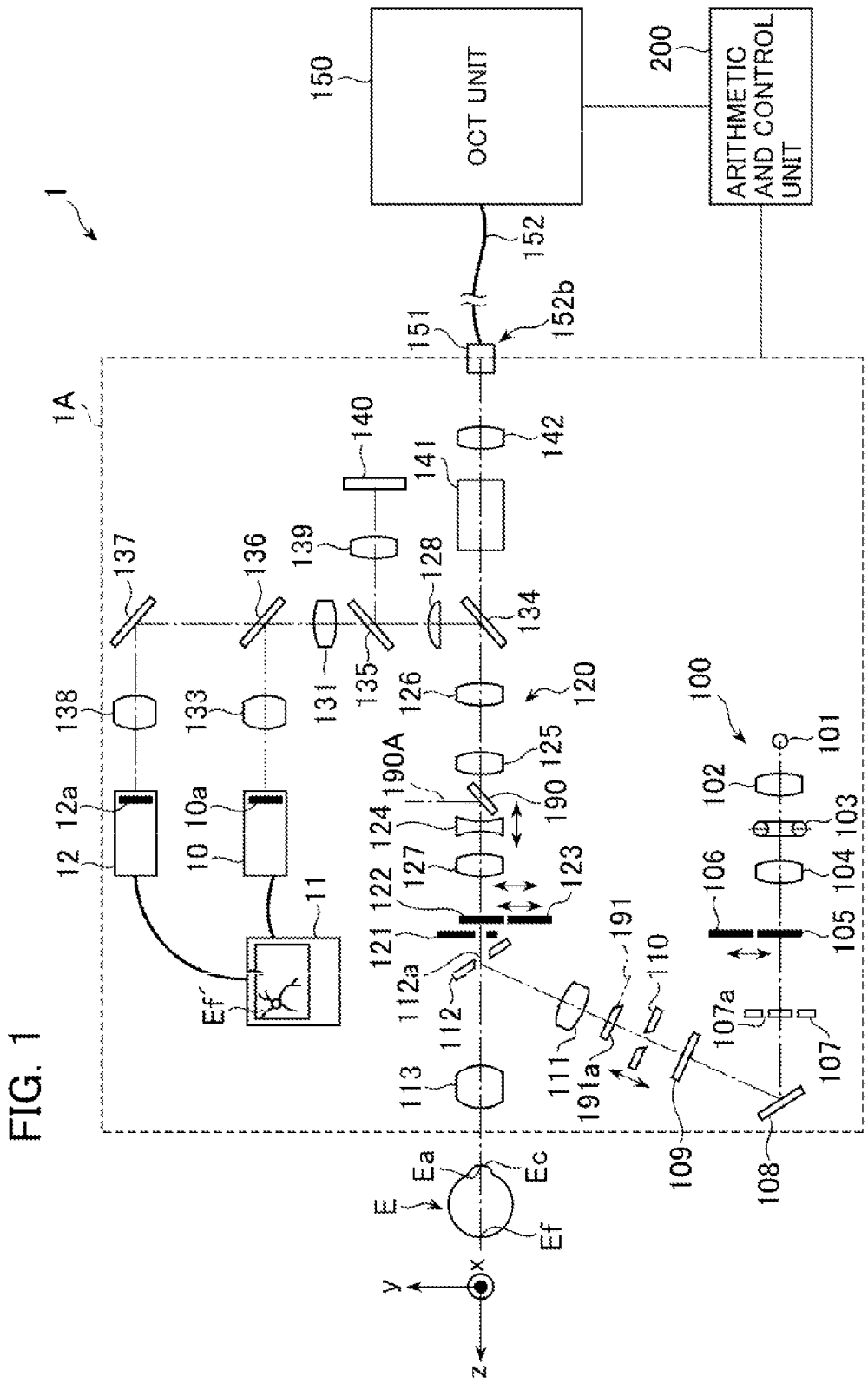
FIG. 1 is a figure showing a configuration of an optical image measuring device according to the present embodiment.

DESCRIPTION OF REFERENCE NUMERALS AND SYMBOLS 1 optical image measuring device
1A retinal camera unit
10 imaging device
10a image pick-up element
11 touch panel monitor
12 imaging device
12a image pick-up element
100 illumination optical system
101 observation light source
102 condenser lens
103 imaging light source
104 condenser lens
105 exciter filter
106 exciter filter
107 ring transparent plate
107a ring slit
108 mirror
109 LCD
110 illumination diaphragm
111 relay lens
112 aperture mirror
112a aperture
113 objective lens
120 imaging optical system
121 imaging diaphragm
122 barrier filter
123 barrier filter
124 focusing lens
125 relay lens
126 imaging lens
127 depth zone switching lens
128 field lens
129 lens insertion/retraction mechanism
131 relay lens
133 imaging lens
134 dichroic mirror
135 half mirror
136 dichroic mirror
137 reflection mirror
138 imaging lens
139 lens
140 LCD
141 scan unit
142 lens
150 OCT unit
151 connector part
152 connection line
152a optical fiber
152b end face
160 low-coherence light source
161 optical fiber
162 optical coupler
163 optical fiber
164 optical fiber
165 optical fiber
171 collimator lens
172 glass block
173 density filter
174a reference mirror
174b reference mirror
175 beam splitter
176a shading plate
176b shading plate
177a light path length switch mechanism
177b light path length switch mechanism
178a reference mirror drive mechanism
178b reference mirror drive mechanism
180 spectrometer
181 collimator lens
182 diffraction grating
183 imaging lens
184 CCD
190 half mirror
190A alignment optical system
190a alignment light source 190b light guide
190c reflection mirror
190d two-hole aperture
190d1 hole
190d2 hole
190d3 central position
190e relay lens
190β emission end
191 focus target projection optical system
191a stick mirror
191a1 reflection face
191b target projection light source
191c pin hole plate
191d lens
191e prism
191f focus target plate
191g two-hole aperture plate
191h lens
191k focus target image
200 arithmetic and control unit
210 controller
220 image forming part
230 image processor
240 display part
250 manipulator
A fundus-oculi conjugate surface
E eye
Ea anterior segment
Ec corneal vertex
Ef fundus oculi
Ef' fundus oculi image
L0 low-coherence light
LC interference light
LR reference light
LRa first reference light
LRb second reference light
LS signal light
Im interference image
M maker
P1 alignment bright point
P2 alignment bright point
S scale
W working distance

BEST MODE FOR CARRYING OUT THE INVENTION

An example of an embodiment of an optical image measuring device according to the present invention will be described in detail with reference to the drawings.

Figure 2:
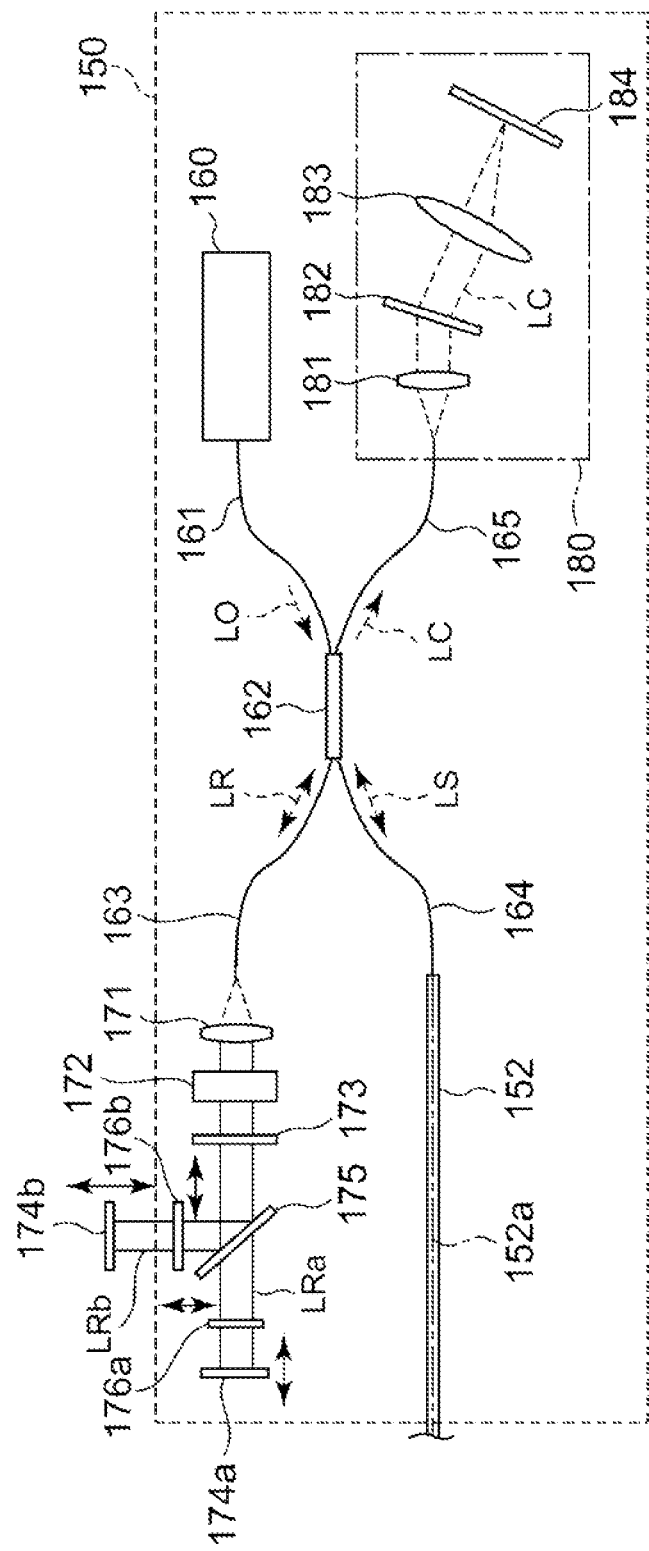
FIG. 2 is a figure showing an optical system of an OCT unit in the optical image measuring device according to the present embodiment.

FIG. 1 is a figure showing a configuration of an optical image measuring device 1 according to the present embodiment. FIG. 2 is a figure showing an optical system of an OCT unit 150 in the optical image measuring device 1.

The optical image measuring device 1 according to the present embodiment is used in the ophthalmologic field to acquire an OCT image of an eye E. The OCT image is a tomographic image or a three-dimensional image of the eye E. A like effect can be obtained by a like configuration also at the time of acquisition of an OCT image of a measured object other than a living eye.

The optical image measuring device 1 includes a configuration to which a Fourier-Domain-type method is applied. To be specific, in this embodiment, the optical image measuring device 1 is provided with almost the same configuration as the device disclosed in the Patent Document 5. In a case that another configuration is applied, application of a similar configuration to that of this embodiment makes it possible to obtain similar actions and effects. For example, it is possible to apply the configuration according to this embodiment to any type of OCT device that scans with a signal light and executes measurement as in the Swept Source type. Besides, it is also possible to apply the configuration according to this embodiment to an OCT technique, such as the full-field type, in which a scan with a signal light is not executed.

An optical image measuring device 1, as shown in FIG. 1, includes a retinal camera unit 1A, an OCT unit 150, and an arithmetic and control unit 200.

The retinal camera unit 1A is a device that photographs the surface of a fundus oculi and acquires its two-dimensional image. Moreover, the retinal camera unit 1A is utilized for photographing the morphology of fundus oculi blood vessels. A two-dimensional image of the fundus oculi surface includes a color image and a monochrome image obtained by photographing the fundus oculi surface and a fluorescent image. A fluorescent image includes a fluorescein angiography image, an indocyanine green angiography image, and so on).

The retinal camera unit 1A provides a part of optical system toward the eye E for the OCT unit 150.

The OCT unit 150 houses an optical system for acquiring an OCT image of an eye E. To the OCT unit 150, one end of a connection line 152 is attached. An optical fiber 152a runs through inside the connection line 152.

To the other end of the connection line 152, a connector part 151 that connects the connection line 152 to the retinal camera unit 1A is attached.

The OCT unit 150 and the retinal camera unit 1A are optically connected via the connection line 152.

The retinal camera unit 1A and the OCT unit 150 have a positional relationship in an optical system that can be photographed respectively by switching a depth zone that is an image target to a different range. The depth zone is a range that is represented by the width of the depth (z direction) in the direction from the anterior segment Ea to the fundus oculi Ef using a corneal vertex Ec as a basis. A depth zone of the anterior segment Ea refers to, for example, a continuous region from the corneal vertex Ec to its edge or a crystalline lens, and a depth zone of the fundus oculi Ef refers to a region of depth into which a retina expands.

The arithmetic and control unit 200 is provided with a computer that executes various arithmetic processes, control processes, and so on. The arithmetic and control unit 200 is connected to both the retinal camera unit 1A and the OCT unit 150 via a communication line that transmits electric signals.

Based on FIG. 1, the retinal camera unit 1A is described in detail.

Like a conventional retinal camera, the retinal camera unit 1A is provided with an illumination optical system 100 and an imaging optical system 120. The illumination optical system 100 radiates an illumination light to the fundus oculi Ef. The imaging optical system 120 leads a fundus oculi reflected light of the illumination light to imaging devices 10 and 12.

The fundus oculi reflected light is a light reflected by the fundus oculi Ef. Moreover, the imaging optical system 120 leads a signal light coming from the OCT unit 150 to the eye E, and also leads the signal light reflected by the eye E to the OCT unit 150. That is, a part of the imaging optical system 120 functions as a part of the optical system for OCT measurement.

As in a conventional retinal camera, the illumination optical system 100 includes an observation light source 101, a condenser lens 102, an imaging light source 103, a condenser lens 104, exciter filters 105 and 106, a ring transparent plate 107, a mirror 108, an LCD (Liquid Crystal Display) 109, an illumination diaphragm 110, a relay lens 111, an aperture mirror 112, and an objective lens 113.

The observation light source 101 outputs an illumination light including a wavelength of an infrared region in the range from about 700 to 800 nm, for example. The condenser lens 102 is an optical element that condenses the illumination light that is emitted from the observation light source 101 and illuminates the illumination light substantially uniformly on the fundus oculi Ef.

The imaging light source 103 outputs an illumination light including a wavelength of a visible region in the range from about 400 to 700 nm, for example. This near-infrared light is set so as to have a shorter wavelength than a light used in the OCT unit 150. The condenser lens 104 is an optical element that condenses the illumination light that is emitted from the imaging light source 103 and illuminates the illumination light substantially uniformly on the fundus oculi Ef.

The exciter filters 105, 106 are filters that are used when a fluorography of a fundus oculi Ef is performed. Each of the exciter filters 105, 106 can be inserted into and removed from a light path by the driving mechanism such as a solenoid, etc. The exciter filter 105 is placed on the light path when performing FAG (fluorescent fundus angiography). The exciter filter 106 is placed on the light path when performing ICG (Indocyanine green fluorescence angiography). Also, when performing a color photograph, the exciter filters 105, 106 are both removed from the light path.

The ring transparent plate 107 is placed in a conjugate position with a pupil of the eye E, and comprises a ring slit 107a centered on the optical axis of the illumination optical system 100. The mirror 108 reflects illumination light that is emitted by the observation light source 101 or an imaging light source 103 towards the optical axis of the imaging optical system 120. The LCD 109 displays fixation targets for fixating the eye E.

The illumination diaphragm 110 is an aperture member that blocks a part of the illumination light to prevent flares, etc. The illumination diaphragm 110 is constructed to be able to move towards the optical axis of the illumination optical system 100; thus, the illuminated region of the fundus oculi Ef can be adjusted.

An aperture mirror 112 is an optical element that synthesizes the optical axis of the illumination optical system 100 and the optical axis of the imaging optical system 120. An aperture 112a is opened in a central region of the aperture mirror 112. The optical axis of the illumination optical system 100 and the optical axis of the imaging optical system 120 intersect at a substantially central position of the aperture 112a.

In said illumination optical system 100, the illumination light that was emitted from the observation light source 101 is projected to the ring transparent plate 107 via the condenser lenses 102 and 104. The light that went through the ring slit 107a of the ring transparent plate 107 is reflected by the mirror 108 and is reflected by the aperture mirror 112 via the LCD 109, the illumination diaphragm 110, and the relay lens 111. The illumination light that is reflected by the aperture mirror 112 advances along the optical axis of the imaging optical system 120 and illuminates the fundus oculi Ef by being focused by an objective lens 113 and entering the eye E.

At this point, because the ring transparent plate 107 is placed in a conjugate position for a pupil of the eye E, a ring-shaped image of the illumination light that enters the eye E is formed on the pupil. A fundus oculi reflection light of the illumination light is emitted from the eye E via a central dark section of the ring-shaped image on the pupil.

When photographing the fundus oculi Ef, the illumination light is emitted as a flash from the imaging light source 103. The illumination light that is emitted from the imaging light source 103 is projected to the fundus oculi Ef by entering the eye E through the condenser lens 104 to the objective lens 113 similar to the illumination light of the observation light source 101.

There is a case in which the illumination light goes through the exciter filter 105 or 106. The exciter filter 105 or 106 is placed selectively in the light path depending on the use of FAG or ICG when conducting fluorography.

The imaging optical system 120 includes the objective lens 113, (an aperture 112a of) the aperture mirror 112, an imaging diaphragm 121, barrier filters 122 and 123, a focusing lens 124, a relay lens 125, an imaging lens 126, a dichroic mirror 134, a field lens 128, a half mirror 135, a relay lens 131, a dichroic mirror 136, an imaging lens 133, the imaging device 10, a reflection mirror 137, an imaging lens 138, the imaging device 12, a lens 139, and an LCD 140. Furthermore, the imaging optical system 120 includes, between the barrier filters 122 and 123 and a focusing lens 124, a depth zone switching lens 127 that can be inserted into and removed from the light path.

The imaging diaphragm 121 is a plate-like member in which a plurality of circular transparent parts of different sizes are formed. A plurality of transparent parts forms apertures with different aperture values and by a driving mechanism, the transparent parts are placed in the light path in alternative ways.

Each of the barrier filters 122 and 123 can be inserted into and removed from a light path by the driving mechanism such as a solenoid, etc.

The barrier filter 122 is placed on the light path when performing FAG and the barrier filter 123 is placed on the light path when performing ICG.

Also, when performing a color photograph, the barrier filters 122 and 123 are both removed from the light path.

The focusing lens 124 can move along the optical axis of the imaging optical system 120 via a slider, etc. The focusing lens 124 is used for fine focus adjustments for the fundus oculi Ef. The imaging optical system 120 is designed such that the fundus oculi Ef is focused when matching the distance between the eye E and the objective lens 113 to a predetermined working distance (hereinafter, a predetermined working distance is referred to as a working distance Wd). The working distance Wd for photographing the fundus oculi Ef is defined such that, for example, the distance between the corneal vertex Ec and the objective lens 113 is 40.7 mm, etc. However, because the diopter of the eye E causes the focus to be off, a fine adjustment is performed by moving this focusing lens 124.

That is, the focusing lens 124 causes the fundus oculi Ef and the end face 152b of the optical fiber 152a to be conjugate by adjusting its placement position along the optical axis of the imaging optical system 120 in accordance with the diopter of the eye E. When the conjugate relationship is established, the signal light LS that goes through the objective lens 113 after being output by the OCT unit 150 is focused on the fundus oculi Ef. Also, the fundus oculi reflection light, including backscattering, is efficiently led to the end face 152b of the optical fiber 152a. That is to say, the focusing lens 124 condenses the signal light LS that goes through the objective lens 113, which is output by the OCT unit 150 at the fundus oculi Ef, and efficiently leads the fundus oculi reflection light, including backscattering, to the end face 152b of the optical fiber 152a.

The depth zone switching lens 127 is a so-called relay lens and can be inserted into and removed from the optical path of the imaging optical system 120 by the driving mechanism of a solenoid, etc. The depth zone switching lens 127 causes the focus to transition from the depth zone of the fundus oculi Ef to the depth zone of the anterior segment Ea.

That is, the depth zone switching lens 127 causes the anterior segment Ea and an end face 152b of the optical fiber 152a to be conjugated by being inserted into the light path of the imaging optical system 120. In other words, the depth zone switching lens 127 condenses a signal light LS that is emitted from the end face 152b of the optical fiber 152a, which is output by the OCT unit 150 on the anterior segment Ea via the objective lens 113. Also, the depth zone switching lens 127 collects the reflection light from the anterior segment Ea including backscattering, to the objective lens 113. As described later, the depth zone switching lens 127 is also used by the retinal camera unit 1A and the OCT unit 150 when photographing the anterior segment Ea.

The dichroic mirror 134 reflects the fundus oculi reflected light of the illumination light output from the illumination optical system 100. The fundus oculi reflected light contains a wavelength included in the range from about 400 to 800 nm. Moreover, the dichroic mirror 134 transmits the signal light LS coming from the OCT unit 150. The signal light LS contains a wavelength included in the range from about 800 to 900 nm, for example.

The dichroic mirror 136 reflects the fundus oculi reflected light of the illumination light coming from the observation light source 101. Moreover, the dichroic mirror 136 transmits the fundus oculi reflected light of the illumination light coming from the imaging light source 103.

The LCD 140 displays an internal fixation target for fixating the eye E. The light from the LCD 140 is focused by the lens 139, reflected by the half mirror 135, propagated through the field lens 128, and reflected by the dichroic mirror 134. Furthermore, this light is propagated through the imaging lens 126, the relay lens 125, the focusing lens 124, the aperture 112a of the aperture mirror 112, the objective lens 113 and so on, and enters the eye E. Consequently, the internal fixation target is projected to the fundus oculi Ef.

By changing a display position of the internal fixation target by the LCD 140, it is possible to change a fixation direction of the eye E. The fixation direction of the eye E is, for example, a fixation direction for acquiring an image centered on the macula of the fundus oculi Ef, a fixation direction for acquiring an image centered on the optic papilla, a fixation direction for acquiring an image centered on the fundus oculi center between the macula and the optic papilla, and so on, as in conventional retinal cameras.

The imaging device 10 includes an image pick-up element 10a. The imaging device 10 functions as an infrared TV camera that detects a near-infrared light. The imaging device 10 detects a near-infrared light and outputs video signals. The image pick-up element 10a is any kind of image pick-up element (area sensor) such as a CCD (Charge Coupled Device) or a CMOS (Complementary Metal Oxide Semiconductor), for example.

The imaging device 12 includes an image pick-up element 12a. The imaging device 12 is specifically capable of detecting a light of a wavelength in the visible region. In other words, the imaging device 12 functions as a TV camera that detects a visible light. The imaging device 12 detects a visible light and outputs video signals. Like the image pick-up element 10a, the image pick-up element 12a is composed of any kind of image pick-up element (area sensor).

A touch panel monitor 11 displays a fundus oculi image Ef based on the video signals from the respective image pick-up elements 10a and 12a.

Moreover, the video signals are transmitted to the arithmetic and control unit 200.

The retinal camera unit 1A is provided with a scan unit 141 and a lens 142. Also, the collimator lens is located in the connector part 151. The collimator lens creates the signal light LS that is emitted from the end face 152b of the optical fiber 152a as a parallel light flux. The lens 142 forms an image of the signal light LS that goes through the scan unit 141 as the parallel light flux on a fundus-oculi conjugate surface A that is a photograph surface of the fundus oculi in the imaging optical system 120 of the retinal camera unit 1A. In addition, the collimator lens condenses the signal light LS that is returned along the imaging optical system 120 and led as a parallel light flux at the end face 152b of the optical fiber 152a.

The scan unit 141 scans a target position on the eye E with the signal light LS output from the OCT unit 150. The scan unit 141 scans with the signal light LS on the xy-plane shown in FIG. 1. For this purpose, the scan unit 141 is provided with, for example, a Galvano mirror for scanning in the x-direction and a Galvano mirror for scanning in the y-direction.

Next, the OCT unit 150 will be described with reference to FIG. 2.

The OCT unit 150 has an optical system like that of a conventional Fourier-Domain-type optical image measuring device. That is to say, the OCT unit 150 has: an optical system that splits a low-coherence light L0 into a reference light LR and a signal light LS and makes the signal light LS propagated through the eye E and the reference light LR reflected by a reference object interfere with each other to generate an interference light LC; and a detector that detects this interference light LC. The result of the detection of the interference light is transmitted to the arithmetic and control unit 200.

A low-coherence light source 160 is a broadband light source that outputs a broadband low-coherence light L0. As this broadband light source, for example, a super luminescent diode (SLD), a light emitting diode (LED) and the like can be used.

For example, the low-coherence light L0 includes a light of a wavelength in the near-infrared region and has a temporal coherence length of about tens of micrometers. The low-coherence light L0 includes a longer wavelength than the illumination light of the retinal camera unit 1A (a wavelength of about 400-800 nm), for example, a wavelength in the range from about 800 to 900 nm.

The low-coherence light L0 output from the low-coherence light source 160 is led to an optical coupler 162 through an optical fiber 161. The optical fiber 161 is composed of, for example, a single mode fiber or a PM (polarization maintaining) fiber.

An optical coupler 162 is a splitter that splits a low-coherence light L0 that goes through a single optical fiber 161 into two optical fibers 163 and 164, and a coupler that superimposes the reference lights LR that go through two of the optical fibers 163 and 164 and the signal light LS.

The reference light LR generated by the optical coupler 162 is led by an optical fiber 163 composed of a single mode fiber or the like, and is emitted from the end face of the fiber. Furthermore, the reference light LR is collimated by a collimator lens 171 and propagated through a glass block 172 and a density filter 173.

Behind the glass block 172 and the density filter 173, a switching part that switches the light path in which the reference light LR goes through to an optical path length corresponding to any of a plurality of depth zones is provided.

The switching part has a beam splitter 175, two reference mirrors 174a and 174b, and shading plates 176a and 176b which are paired with the reference mirrors 174a and 174b.

The reference light LR transmitted through the density filter 173 is split into the first reference light LRa and the second reference light LRb by the beam splitter 175. The beam splitter 175 is composed of a half mirror, for example.

Each of the reference mirrors 174a and 174b is placed by orthogonalizing their mirror surfaces to the light path. The reference mirror 174a is in the light path of a first reference light LRa and reflects the first reference light LRa back to its original light path. The reference mirror 174b is in the light path of the second reference light LRb and reflects the second reference light LRb back to its original light path.

The reference mirrors 174a and 174b is movable in travelling directions of first and second reference lights LRa and LRb, respectively.

Thus, in accordance with the axial length of the eye E, the working distance and so on, it is possible to ensure the optical path lengths of the first and second reference lights LRa and LRb. Moreover, by moving the respective reference mirrors 174a and 174b, it is possible to measure various depth positions of the eye E.

The optical path via the reference mirror 174a is referred to as a first optical path, and the optical path via the reference mirror 174b is referred to as a second optical path. The reference mirrors 174a and 174b are arranged so that the optical path length of the first optical path and the optical path length of the second optical path are different. That is to say, the reference mirrors 174a and 174b are mounted so that distances to the beam splitter 175 are different from each other.

For example, the reference mirror 174a is placed such that the first light path almost equals the optical path length of the signal light LS, which reaches the fundus oculi Ef that includes a retina. The reference mirror 174b is placed such that the second light path almost equals the optical path length of the signal light LS, which reaches the anterior segment Ea that includes a cornea. This placement position is defined in advance, corresponding to the working distance.

That is, the first light path via the reference mirror 174a is a light path that adjusts the optical path length of the reference light LR to obtain OCT images of the fundus oculi Ef as the first depth zone. The second light path via reference mirror 174b is a light path that adjusts the optical path length of the reference light LR to obtain OCT images of the anterior segment Ea as the second depth zone.

The shading plates 176a and 176b are reflection-free terminations such as black bodies, etc. and light shielding members that shield light. Each of the shading plates 176a and 176b can be inserted into and removed from the corresponding light paths by a drive unit such as a solenoid. The shading plate 176a is paired with the reference mirror 174a and can be inserted into and removed from the first light path. The shading plate 176b is paired with the reference mirror 174b and can be inserted into and removed from the second light path.

Either one of the shading plates 176a or 176b stands in the corresponding light path and blocks either one of the first reference light LRa or the second reference light LRb, which goes through its light path. When measuring the fundus oculi Ef as the first depth zone, the second reference light LRb is blocked by inserting the shading plate 176b into the second light path. When measuring the anterior segment Ea as the second depth zone, the first reference light LRa is blocked by inserting the shading plate 176a into the first light path.

In this switching part, the first reference light LRa that is generated from the beam splitter 175, if the shading plate 176a is not inserted, returns to the beam splitter 175 after being reflected from the reference mirror 174a.

On the other hand, the second reference light LRb that is generated by the beam splitter 175, if the shading plate 176b is not inserted, returns to the beam splitter 175 after being reflected by the reference mirror 174b. Because either one of the shading plates 176a or 176b is inserted into the light path, only one of the first reference light LRa or the second reference light LRb returns to the beam splitter 175.

One of the reference lights LRa and LRb returned to the beam splitter 175 is propagated through the density filter 173 and the glass block 172 again, focused to the fiber end face of the optical fiber 163 by the collimator lens 171, and led to the optical coupler 162 through the optical fiber 163.

The glass block 172 and the density filter 173 act as a delaying means that makes the optical path lengths of the reference light LR and the signal light LS match each other. Moreover, the glass block 172 and the density filter 173 act as a dispersion compensating means that makes the dispersion properties of the reference light LR and the signal light LS match each other.

Further, the density filter 173 acts as a neutral density filter that reduces the light amount of the reference light LR. The density filter 173 is composed of, for example, a rotary-type ND (Neutral Density) filter. The density filter 173 is driven to rotate by a driving mechanism that is not shown in the drawings, thereby changing the light amount of the reference light LR that contributes to generation of the interference light LD.

On the other hand, the signal light LS generated by the optical coupler 162 is led to the end of the connection line 152 through an optical fiber 164 composed of a single mode fiber or the like. The optical fiber 164 and the optical fiber 152a may be composed of one optical fiber, or may be integrally formed by joining the end faces of the respective fibers.

The signal light LS is led by the optical fiber 152a, emitted from the end surface 152b, and guided to the retinal camera unit 1A. The signal light LS that is emitted from the end face 152b of the optical fiber 152a becomes a parallel light flux via the collimator lens, goes through the scan unit 141, and is condensed at the fundus-oculi conjugate surface A by the lens 142.

Furthermore, the signal light LS is propagated through the dichroic mirror 134, the imaging lens 126, the relay lens 125, the half mirror 190, the focusing lens 124, the imaging diaphragm 121, the aperture 112a of the aperture mirror 112 and the objective lens 113, and radiated to the eye E.

When projecting the signal light LS to the anterior segment Ea that includes a cornea, in other words, when projecting the signal light LS in the second depth zone, the depth zone switching lens 127 is inserted into the light path in advance. Moreover, when the signal light LS is radiated to the eye E, the barrier filters 122 and 123 are retracted from the optical path in advance.

At this moment, the half mirror 190 may also be retracted from the optical path.

The signal light LS reflected by the eye E is guided reversely on the same path as the signal light LS travelling to the eye E, and if the signal light LS is emitted as a parallel light flux from the lens 142, it is focused on the end face 152b of the optical fiber 152a. Moreover, the signal light LS enters the OCT unit 150 through the optical fiber 152a, and returns to the optical coupler 162 through the optical fiber 164.

The signal light LS having entered the eye E is reflected at various sites of the eye E. For example, the signal light LS is reflected at the anterior segment Ea and fundus oculi Ef such as the cornea, the crystalline lens, the retina, and so on. At this moment, the signal light LS is not only reflected at the front faces of the anterior segment Ea and the fundus oculi Ef but also scattered at a refractive index boundary of the deep part. For example, the signal light LS is reflected not only at the front face of the cornea Ec but also at the back face of the cornea Ec and the layer of the cornea cell. Moreover, the signal light LS is reflected not only at the retinal surface of the fundus oculi Ef but also the boundary of cell layers composing the retina, the boundary between the retina and the choroidea, and so on. Moreover, the signal light LS is reflected not only at the front face of the crystalline lens but also at the back face thereof. Therefore, the signal light LS reflected by the eye E includes information that reflects the morphology of the front and back faces of various sites of the eye E, and information that reflects a state of back scatter at the refractive index boundary of the deep tissues.

However, when the distance between the corneal vertex Ec and the objective lens 113 is matched to the working distance Wd using an alignment optical system 190A and a focus target projection optical system 191, which are described later, and the placement position of the focusing lens 124 is adjusted, the signal light LS that is emitted from the OCT UNIT 150 is condensed at the fundus-oculi conjugate surface A and is condensed on the fundus oculi Ef through the imaging lens 126, the relay lens 125, the focusing lens 124, and the objective lens 113.

In addition, when the distance between the corneal vertex Ec and the objective lens 113 is matched to the working distance Wd, the focusing lens 124 is returned to a predetermined position, and the depth zone switching lens 127 is inserted into the light path, the signal light LS via relay lens 125 after entering the imaging lens 126 is condensed on the anterior segment Ea by adjusting the light path by the focusing lens 124 and the depth zone switching lens 127 and the objective lens 113. Also, at this point, the signal light LS that is reflected by the anterior segment Ea is condensed at the end face 152b of the optical fiber 152a using the collimator lens after adjusting the light path by the objective lens 113, the depth zone switching lens 127 and the focusing lens 124, entering the lens 142 via the relay lens 125 and the imaging lens 126, becoming a parallel light flux. That is, backscattering from the boundary of a reflective index of the anterior segment Ea becomes the main body of the signal light LS at this point.

The optical coupler 162 makes the signal light LS having returned after reflected by the eye E interfere with the reference light LR having returned after reflected by the reference mirror 174a or 174b to generate the interference light LC. The interference light LC is generated by superimposing and interfering the signal light LS and the reference light LR by the optical coupler 162. The interference light LC is led to a spectrometer 180 through an optical fiber 165 composed of a single mode fiber or the like.

The spectrometer 180 detects the spectral components of the interference light LC. The spectrometer 180 includes a collimator lens 181, a diffraction grating 182, an imaging lens 183, and a CCD 184. The diffraction grating 182 may be either a transmission-type or a reflection-type. Moreover, it is also possible to use another photodetecting device (an area sensor) such as a CMOS, instead of the CCD 184.

The interference light LC having entered the spectrometer 180 is collimated by the collimator lens 181, and divided into spectra by the diffraction grating 182. The divided interference light LC is formed into an image on the image pick-up face of the CCD 184 by the imaging lens 183.

The CCD 184 detects the respective spectral components of the divided interference light LC and converts the components into electric charges. The CCD 184 accumulates these electric charges and generates detection signals. Furthermore, the CCD 184 transmits these detection signals to the arithmetic and control unit 200. The spectrometer 180 (specifically, the CCD 184) is an example of a "detector" of the present invention.

Although a Michelson-type interferometer is employed in this embodiment, it is possible to employ any type of interferometer such as a Mach-Zehnder-type as necessary.

Figure 3A:
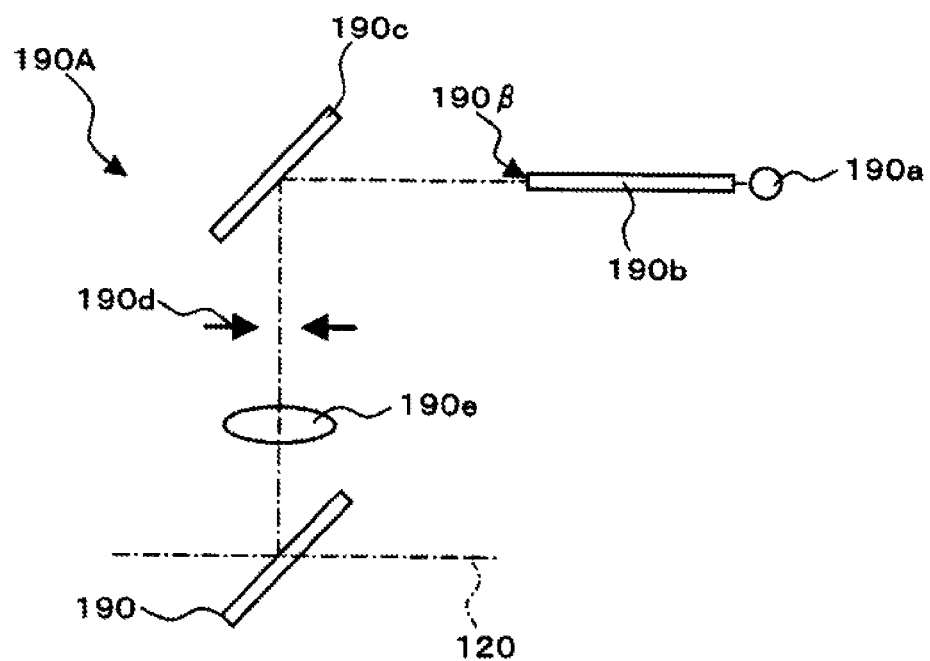
FIG. 3A is a figure showing an alignment optical system of the optical image measuring device according to the present embodiment.
Figure 3B:
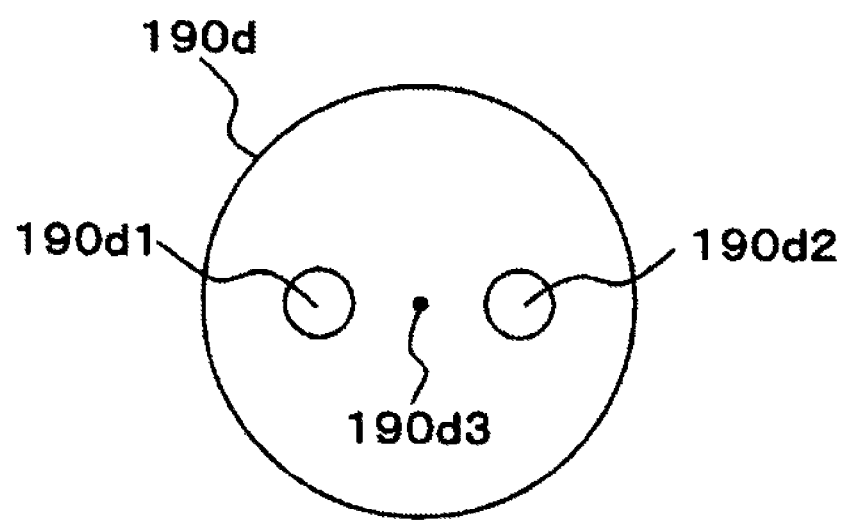
FIG. 3B is a figure showing an alignment optical system of the optical image measuring device according to the present embodiment.
Figure 4:
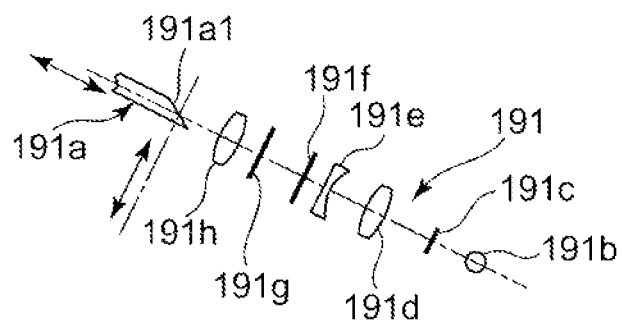
FIG. 4 is a figure showing a focus target projection optical system of the optical image measuring device according to the present embodiment.

In this optical image measuring device 1, in order to obtain vivid OCT images of desired depth zones, it is important to perform the alignment adjustment and the focus adjustment. FIGS. 3A and 3B are figures showing an alignment optical system 190A of the optical image measuring device 1. FIG. 4 is a figure showing a focus target projection optical system 191 of the optical image measuring device 1.

First, the alignment optical system 190A will be described based on FIGS. 3A and 3B.

On an optical path between the focusing lens 124 and the relay lens 125, a half mirror 190 is formed at a slant. The half mirror 190 acts to compose an optical path of an alignment optical system 190A shown in FIG. 3A and the optical path of the imaging optical system 120. The alignment optical system 190A is an optical system for position matching of the optical system with respect to the eye E when measuring the fundus oculi Ef of the eye E.

An alignment bright point is used for both an alignment in the xy-direction and an alignment in the z-direction. The alignment adjustment in the xy-direction is to make a corneal vertex Ec of the eye E match the optical axes of the optical systems 100 and 120. The alignment adjustment in the z-direction is to make the distance between the eye E and the objective lens 113 match the working distance WD.

The alignment optical system 190A, as shown in FIG. 3A, includes the half mirror 190, an alignment light source 190a, a light guide 190b, a reflection mirror 190c, a two-hole aperture 190d, and a relay lens 190e. The alignment light source 190a, for example, includes a light source such as an LED that outputs an alignment light. The alignment light is a light of near-infrared region.

The two-hole aperture 190d has two holes 190d1 and 190d2 as shown in FIG. 3B. The holes 190d1 and 190d2 are formed in symmetrical positions with respect to a center position 190d3 of the disk-like two-hole aperture 190d, for example. The two-hole aperture 190d is mounted so that the center position 190d3 is located on the optical path of the alignment optical system 190A.

The alignment light emitted from an emission end 190β of the light guide 190b is reflected by the reflection mirror 190c and led to the two-hole aperture 190d. The alignment light having passed through the holes 190d1 and 190d2 of the two-hole aperture 190d is propagated through the relay lens 190e, reflected by the half mirror 190, and led to the aperture mirror 112. At this moment, the relay lens 190e performs intermediate imaging of an image of the emission end 190β of the light guide 190b in the center position of the aperture 112a of the aperture mirror 112. The center position corresponds to a position on the optical axis of the imaging optical system 120. The alignment light having passed through the aperture 112a of the aperture mirror 112 is projected to the cornea of the eye E via the objective lens 113.

Here, in a case that a positional relation between the corneal vertex Ec and the objective lens 113 coincides with the working distance Wd, and the optical axis of the optical system of the retinal camera unit 1A matches the axis of the eye E, two alignment light fluxes formed by the two-hole aperture 190d are projected to the eye E so as to respectively form images at intermediate positions between the corneal apex Ec and the corneal curvature center.

Next, the focus target projection optical system 191 will be described based on FIG. 4.

In the light path of the illumination optical system 100, a stick mirror 191a that forms a part of the focus target projection optical system 191 is located in a way that allows it to be inserted into and removed from a position which is optically conjugate with the fundus oculi Ef of the eye E. The focus target projection optical system 191 is used for adjusting the focus. The stick mirror 191a is a so-called target stick.

The focus target projection optical system 191 has a target projection light source 191b, a pin hole plate 191c, a lens 191d, a prism 191e, a focus target plate 191f, a two-hole aperture plate 191g, and a lens 191h, in this order. Then, target light from the target projection light source 191b reaches the prism 191e by passing through the pin hole plate 191c and the lens 191d, reaches reflection face 191a1 of the stick mirror 191a by going through the focus target plate 191f, the two-hole aperture plate 191g, and the lens 191h from the prism 191e, and is projected on the fundus oculi Ef of the eye E by passing through the relay lens 111, the aperture mirror 112, and the objective lens 113.

The reflection face 191a1 and the focus target plate 191f of the stick mirror 191a are conjugate. Furthermore, the target light from the target projection light source 191b is separated into two by functions of the prism 191e and the two-hole aperture plate 191g, etc. If the fundus oculi Ef of the eye E and the reflection face 191a1 of the stick mirror 191a are not conjugate, focus target images 191k, which are described later, appear to be separated into two on the left and right.

The stick mirror 191a is located in a way that allows it to be inserted and removed at the light path of the illumination optical system 100 such that the reflection face 191a1 stands in the light path. Also, the focus target projection optical system 191 moves along the optical axis of the illumination optical system 100 such that the focus target plate 191f and the fundus oculi Ef become optically conjugate.

In addition, this focus target projection optical system 191 moves by interlocking the focusing lens 124. The focus target projection optical system 191 and the focusing lens 124 move by interlocking such that the fundus oculi Ef, the reflection face 191a1 of the stick mirror 191a, the image pick-up element 10a or 12a, and the end face 152b of the optical fiber 152a always become optically conjugate. For example, as an interlocking mechanism of the focus target projection optical system 191 and the focusing lens 124, a cogwheel interlocking mechanism using gears may be used. Therefore, by moving the focusing lens 124 using a focus target as a target, the focus can be adjusted easily.

Figure 5:
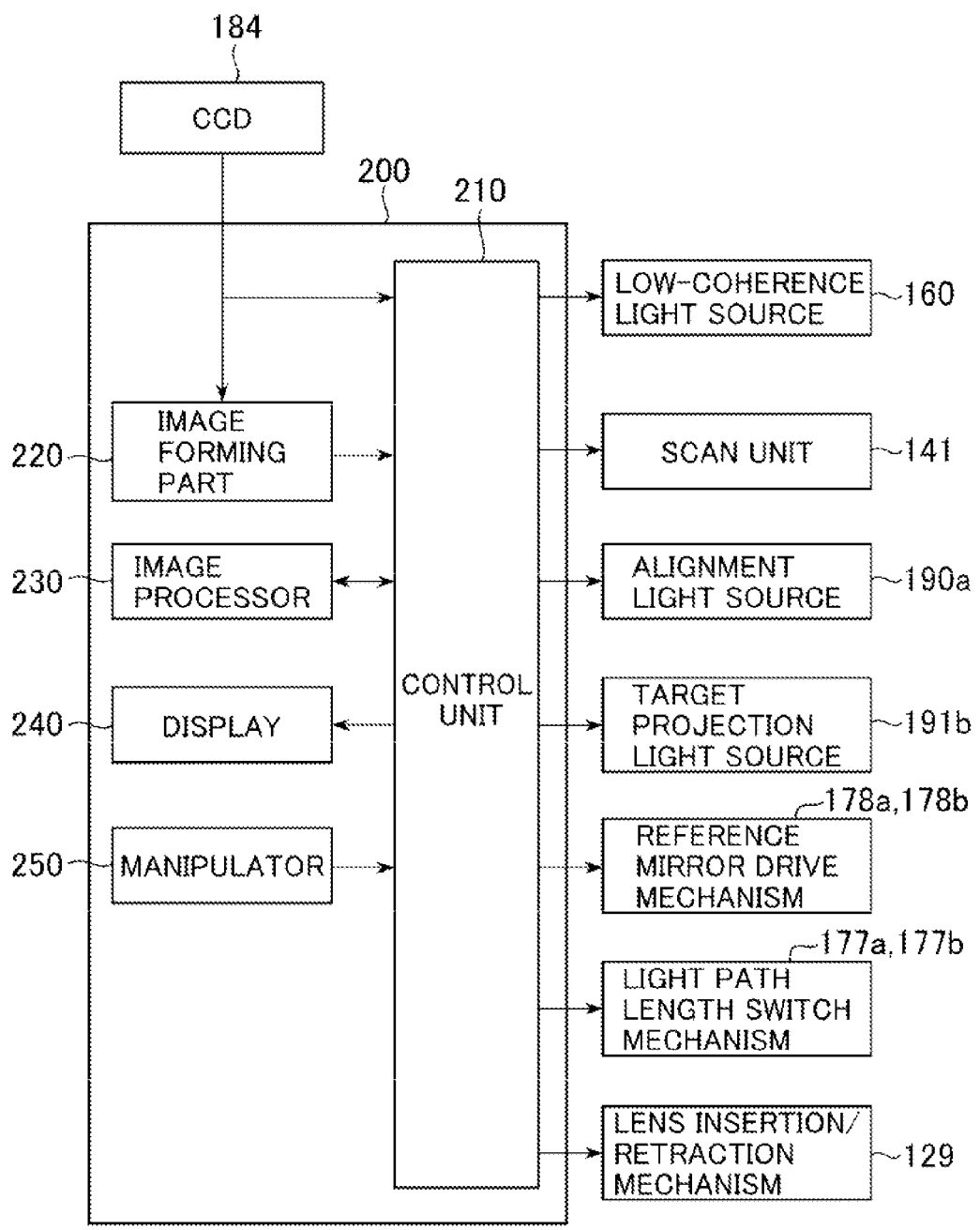
FIG. 5 is a figure showing a configuration of an arithmetic and control unit of the optical image measuring device according to the present embodiment.

The retinal camera unit 1A and the OCT unit 150 are controlled by the arithmetic and control unit 200. FIG. 5 is a block diagram showing a configuration of the arithmetic and control unit 200.

The arithmetic and control unit 200 will be described in detail based on FIG. 5.

The arithmetic and control unit 200 includes a controller 210, an image forming part 220, an image processor 230, a display part 240, and a manipulator 250.

The controller 210, the image forming part 220, and the image processor 230 include a microprocessor, a RAM, a ROM, a hard disk drive, a communication interface, and so on, as in conventional computers. The hard disk drive in the controller 210 stores a computer program for controlling the optical image measuring device 1. The image forming part 220 may be provided with a circuit board dedicated for forming OCT images based on detection signals from the CCD 184.

The display part 240 is a monitor such as a CRT display or a liquid crystal display. The display part 240 visualizes an image after receiving a scanning signal of the image from the controller 210. The manipulator 250 is a man-machine input interface such as a keyboard, a mouse, or a joystick.

The manipulator 250 includes buttons such as a start-up button, a start button, or a mode selection button and outputs an operation signal that corresponds to a press of these buttons toward the controller 210.

The controller 210 controls the optical image measuring device 1 with a press of the start-up button or the start button located in the manipulator 250 and causes OCT images of each depth zone to be obtained in order of selected modes. As selectable modes, a fundus oculi anterior segment mode that causes OCT images of the anterior segment Ea to be obtained continuously after OCT images of the fundus oculi Ef are obtained, and an anterior segment fundus oculi mode that causes OCT images of the fundus oculi Ef to be obtained continuously after OCT images of the anterior segment Ea are obtained.

As control of the retinal camera unit 1A, the controller 210 executes: control of output of the illumination lights by the observation light source 101 and the imaging light source 103; control of insertion/retraction of the exciter filters 105, 106, the barrier filters 122, 123 and the depth zone switching lens 127 to/from the optical path; control of the operation of a display device such as the LCD 140; control of turning on/off of the alignment light source 190a; control of movement of the illumination diaphragm 110 (control of the aperture value); control of alignment adjustment of matching the distance between the corneal vertex Ec and the objective lens 113 with the working distance Wd; control of the aperture value by moving the illumination diaphragm 110; control of the aperture value of the imaging diaphragm 121; control of movement of the focusing lens 124 (control of the magnification); control of correction of refractive power by moving the focusing lens 124; and so on. Furthermore, the arithmetic and control unit 200 controls the scan unit 141 to scan with the signal light LS.

Further, as control of the OCT unit 150, the controller 210 executes: control of output of the low-coherence light L0 by the low-coherence light source 160; control of switching of the optical path length of the reference light LR by selective insertion and retraction of the shading plate 176a, 176b; control of movement of each of the reference mirrors 174a and 174b; control of the rotation operation of the density filter 173 (an operation to change the reduction amount of the light amount of the reference light LR); control of a time for electric charge accumulation, the timing for electric charge accumulation and the timing for signal transmission by the CCD 184; and so on.

The controller 210 synchronously controls the insertion/retraction of the depth zone switching lens 127 into/from the optical path and switching of the optical path length of the reference light LR by the selective insertion and retraction of the shading plate 176a, 176b.

As a control aspect of the controller 210, a drive signal is output to a low-coherence light source 160, light path length switch mechanisms 177a, 177b, a lens insertion/retraction mechanism 129, reference mirror drive mechanisms 178a, 178b, and the scan unit 141 to control.

In particular, in the optical image measuring device 1, light path length switch mechanisms 177a and 177b are set up. The light path length switch mechanism 177a is constructed by including an actuator such as a solenoid that inserts and removes the shading plate 176a into and from the light path. The light path length switch mechanism 177b is constructed by including an actuator such as a solenoid that inserts or removes the shading plate 176b into or from the light path. When the light path length switch mechanism 177a and 177b are constructed with a solenoid, shading plates 176a and 176b are individually connected to a moving core of the solenoid directly or via a transfer mechanism and are inserted into and removed from the light path by an extrusion or withdrawing of the moving core.

The controller 210, when obtaining OCT images of the fundus oculi Ef, outputs a drive signal to the light path length switch mechanism 177b and causes the shading plates 176b to be inserted into the second light path. When the other shading plate 176a is inserted into the light path, the drive signal is output to the light path length switch mechanism 177a and the shading plate 176a that is already inserted is retracted from the first light path.

Also, the controller 210, when obtaining OCT images of the anterior segment Ea, outputs the drive signal to the light path length switch mechanism 177a and inserts the shading plate 176a into the first light path.

When the other shading plate 176b is inserted into the second light path, the drive signal is output to the light path length switch mechanism 177b and the shading plate 176b that is already inserted is retracted from the second light path.

When obtaining OCT images of the anterior segment Ea continuously after obtaining OCT images of the fundus oculi Ef or vice versa, the controller 210 controls the shading plate 176a or 176b that is inserted into the light path alternatively as mentioned above.

Also, in the optical image measuring device 1, a lens insertion/retraction mechanism 129 is placed. The lens insertion/retraction mechanism 129 is constructed including an actuator such as a solenoid that inserts and removes the depth zone switching lens 127 into and from the light path. When the lens insertion/retraction mechanism 129 is a solenoid, the depth zone switching lens 127 is connected directly to the moving core of the solenoid or via the transfer mechanism and is inserted into and removed from the light path by an extrusion or withdrawing of the moving core.

The controller 210, when obtaining OCT images of the fundus oculi Ef and if the depth zone switching lens 127 is inserted into the light path, outputs the drive signal to the lens insertion/retraction mechanism 129 and retracts the depth zone switching lens 127 from the light path. Also, the controller 210, when obtaining OCT images of the anterior segment Ea, outputs the drive signal to the lens insertion/retraction mechanism 129 and inserts the depth zone switching lens 127 into the light path.

When obtaining OCT images of the anterior segment Ea continuously after obtaining OCT images of the fundus oculi Ef, the controller 210 causes to obtain OCT images while the depth zone switching lens 127 is removed from the light path, and after this OCT measurement, causes the depth zone switching lens 127 to be inserted into the light path and obtain OCT images in that state. In contrast, when obtaining OCT images of the fundus oculi Ef continuously after obtaining OCT images of the anterior segment Ea, the controller 210 causes the depth zone switching lens 127 to be inserted into the light path and obtain OCT images in that state, and after this OCT measurement, causes the depth zone switching lens 127 to be removed from the light path and obtain OCT images in that state.

In addition, in the optical image measuring device 1, reference mirror drive mechanisms 178a, 178b are placed. The reference mirror drive mechanism 178a causes the reference mirror 174a to move in the travelling direction of the first reference light LRa. The reference mirror drive mechanism 178b causes the reference mirror 174b to move in the travelling direction of the second reference light LRb.

Each of reference mirror drive mechanisms 178a and 178b is constructed including the actuator and the transfer mechanism. The actuator is constructed by, for example, a pulse motor and generates a drive force that corresponds to its pulse number. The transfer mechanism is constructed including, for example, a gear, etc. and transmits the drive force that is generated by the actuator to the reference mirrors 174a and 174b.

The controller 210 controls scanning of the signal light LS by the scan unit 141.

The scan aspect of the signal light LS by the optical image measuring device 1 is, for example, a horizontal scan, vertical scan, cruciform scan, radial scan, circular scan, concentric scan, and helical scan. These scan aspects are selectively used as necessary in consideration of an observation site of the fundus oculi Ef and the anterior segment Ea, an analysis target such as the retinal thickness or the like, a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between scanning lines to be sufficiently narrow, it is possible to form the aforementioned three-dimensional image (three-dimensional scan).

A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory.

With the configuration as described before, the scan unit 141 is capable of scanning with the signal light. LS in the x-direction and the y-direction, respectively, and is therefore capable of scanning with the signal light LS along any sort of trajectory on the xy-plane. Thus, it is possible to realize various types of scan aspects as described above.

By scanning with the signal light LS in the aspects as described above, it is possible to form a tomographic image in the depth direction along a scanning line (a scanning trajectory). Moreover, in a case that the interval between scanning lines is narrow, it is possible to form the aforementioned three-dimensional image.

The image forming part 220 forms OCT images of the eye E by analyzing the detection signals from the CCD 184.

In particular, when the focus is on the first depth zone that is equivalent to the fundus oculi Ef and the optical path length of the reference light LR is switched by the switching part corresponding to the optical path length of the signal light LS that is reflected at this first depth zone, the image forming part 220 forms OCT images of the fundus oculi Ef. Also, when the focus is on the second depth zone that is equivalent to the anterior segment Ea that includes a cornea and the optical path length of the reference light LR is switched by the switching part corresponding to the optical path length of the signal light LS that is reflected at this second depth zone, the image forming part 220 forms OCT images of the anterior segment Ea.

To form an OCT image, an operating process, even if it is an OCT image of the fundus oculi Ef or an OCT image of the anterior segment Ea, is the same as a conventional Fourier domain type optical image measuring device. Like the conventional Fourier-Domain OCT technique, this process includes processes such as noise elimination (noise reduction), filtering, and FFT (Fast Fourier Transform).

The image processor 230 executes various image processing and analysis processes on the images formed by the image forming part 220. For example, the image processor 230 executes various correction processes such as luminance correction and dispersion correction of images. Further, the image processor 230 executes an interpolation process of interpolating pixels between tomographic images formed by the image forming part 220, thereby forming image data of a three-dimensional image of the fundus oculi Ef.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display part 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a single three-dimensional coordinate system.

Various operation examples of the optical image measuring device 1 will be described.

The flow charts shown in FIG. 6A and FIG. 6B represent examples of the first operation of the optical image measuring device 1 when it is in the fundus oculi anterior segment mode that measures the anterior segment Ea using an optical imaging measurement technology after measuring the fundus oculi Ef using the optical imaging measurement technology.

Figure 7A:
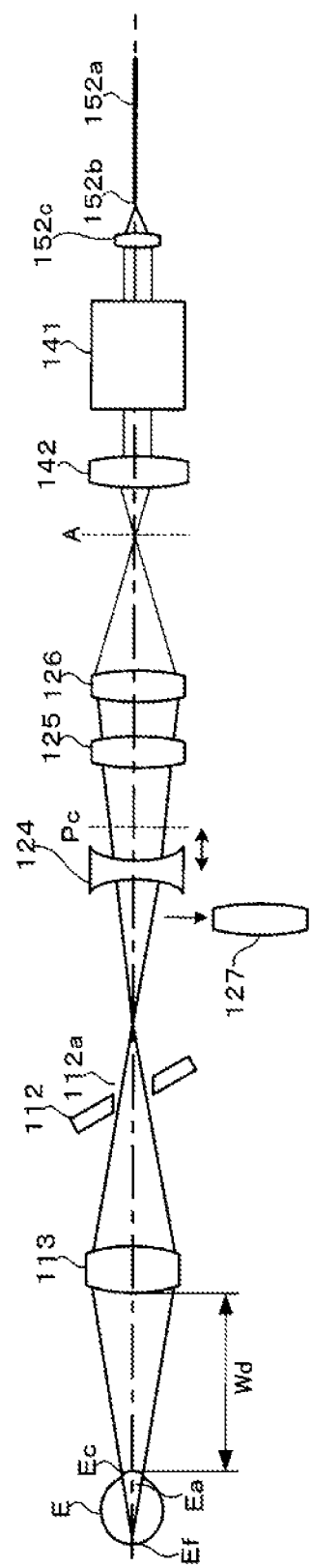
FIG. 7A is a figure showing the first aspect in the operation of the optical image measuring device according to the present embodiment.

Firstly, the controller 210 accepts the selection operation that is in the fundus oculi anterior segment mode via a press of the mode selection button that is located in the manipulator 250 (S01). With the selection of this fundus oculi anterior segment mode, the controller 210 outputs the drive signal to the lens insertion/retraction mechanism 129 and, as shown in FIG. 7A, removes the depth zone switching lens 127 from the light path of the imaging optical system 120 (S02).

Then, the controller 210 controls the alignment of the optical system for the eye E (S03).

For the control of the alignment, the controller 210 causes the alignment light source 190a of an alignment optical system 190A to turn on.

Figure 8A:
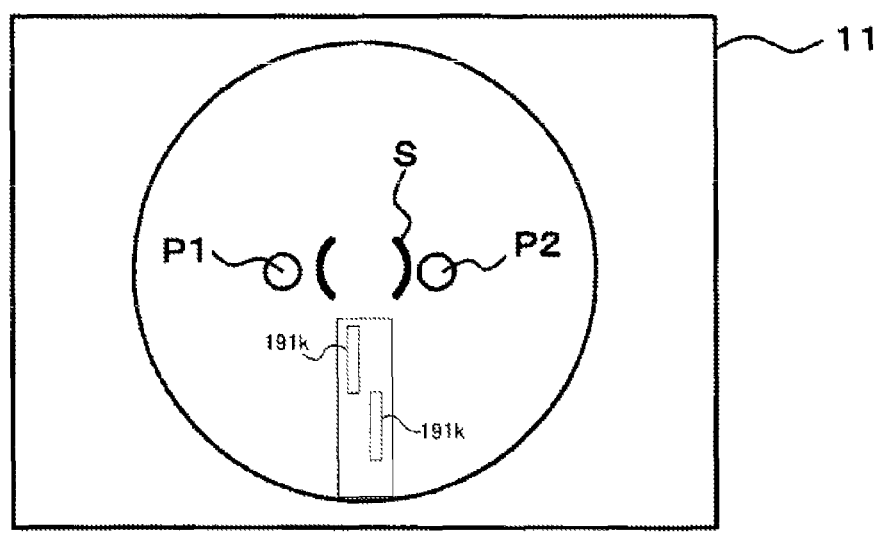
FIG. 8A is a figure showing a display aspect of alignment and focus adjustment of the optical image measuring device according to the present embodiment.
Figure 8B:
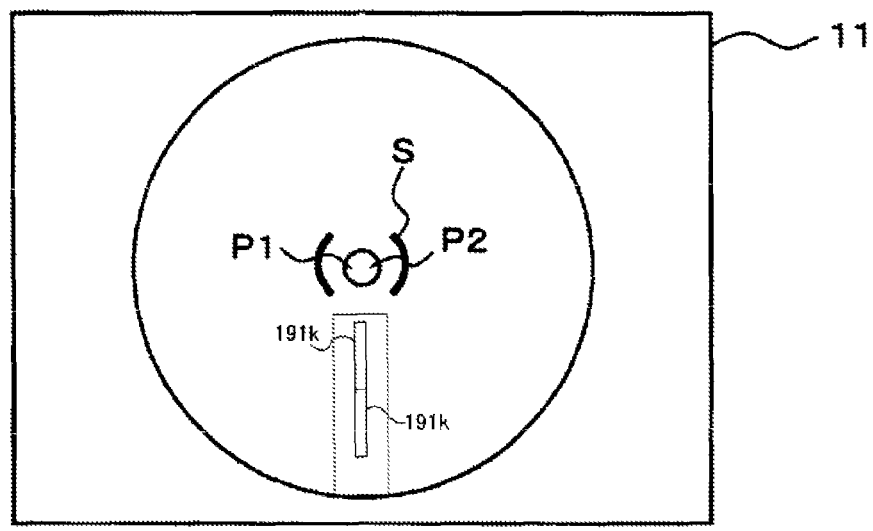
FIG. 8B is a figure showing a display aspect of alignment and focus adjustment of the optical image measuring device according to the present embodiment.

Two alignment light fluxes that go through the two-hole aperture 190d are projected to the cornea via the objective lens 113. The cornea reflected lights are received by, for example, an image pick-up element 10a via the imaging optical system 120. Images captured by the image pick-up elements 10a are displayed on the touch panel monitor 11 or the display part 240. A display aspect of the alignment light in this case is shown in FIGS. 8A and 8B.

The alignment is executed by adjusting the position of the retinal camera unit 1A while projecting the alignment bright points P1 and P2 to the eye E and observing their condition, as shown in FIG. 8.

On the touch panel monitor 11 or the display part 240, a scale S with a bracket shape is displayed in advance. The scale S is displayed such that its central position matches the optical axis of the imaging optical system 120.

The alignment bright points P1 and P2 are displayed in this display state. The alignment bright points P1 and P2 are light reception images of two alignment light fluxes.

As shown in FIG. 8A, when alignment bright points P1 and P2 are displayed at positions that are out of the scale S, the position of the eye E and the position of the retinal camera unit 1A are out of alignment towards the x-direction and/or the y-direction. The up and down directions on the display screen correspond to the y-direction and the right and left directions correspond to the x-direction. In contrast, when the positions of the eye E and the retinal camera unit 1A in the x-direction and the y-direction match each other, the alignment bright points P1 and P2 are displayed in the scale S, as shown in FIG. 8B.

Also, when the alignment bright points P1 and P2 are displayed individually in separate positions, the distance between the corneal vertex Ec and the objective lens 113 is different from the working distance Wd. In contrast, when the alignment bright points P1 and P2 are displayed such that they overlap each other, the distance between the corneal vertex Ec and the objective lens 113 is equal to the working distance Wd.

The examiner executes alignment by adjusting the positional relation between the eye E and the retinal camera unit 1A. The adjustment of the positional relation between the eye E and the retinal camera unit 1A is executed by moving the optical system of the retinal camera unit 1A on a movable table by operating the joystick in the manipulator as in a conventional retinal camera for example.

As a result of this alignment adjustment, the signal light LS is focused on the fundus oculi Ef and the reflection light and backscattering from the fundus oculi Ef are focused on the end face 152b of the optical fiber 152a.

Then, the controller 210 controls the focus for the eye E (S04).

The controller 210 inserts a stick mirror 191a of the focus target projection optical system 191 into the middle of the light path of the illumination optical system 100 and lights the target projection light source 191b. The stick mirror 191a that stands in the light path is projected as a shadow on the fundus oculi Ef by the illumination light of the illumination optical system 100. Also, a light flux that goes through the focus target plate 191f after emitting the target projection light source 191b is separated into two light fluxes due to the function of the two-hole aperture 191g and is projected as a focus target light flux on the fundus oculi Ef via the objective lens 113, etc. after forming an image at the reflection face 191a1 of the stick mirror 191a once.

The focus target light flux and the shadow of the stick mirror 191a that are projected by this fundus oculi Ef is received by, for example, an image pick-up element 10a via the imaging optical system 120. Captured images by the image pick-up element 10a are displayed on the touch panel monitor 11 or the display part 240. A display aspect of the focus target light flux in this situation is shown in FIGS. 8A and 8B.

As shown in FIG. 8A, if the fundus oculi Ef of the eye E and the reflection face 191a1 of the stick mirror 191a are not conjugate, the focus target images 191k by the focus target light flux appear to be separated into two on the right and left. This is because the reflection face 191a1 of the stick mirror 191a and the focus target plate 191f are conjugate. At this point, if the stick mirror 191a is not at the position where the fundus oculi Ef of the eye E and the reflection face 191a1 of the stick mirror 191a are conjugate, because the focusing lens 124 is also not in the position where the fundus oculi Ef of the eye E, the image pick-up element 10a, etc. and the end face 152b of the optical fiber 152a are conjugate, the focus is not on the fundus oculi Ef.

As shown in FIG. 8B, when the fundus oculi Ef of the eye E and the reflection face 191a 1 of the stick mirror 191a are conjugates, two focus target images 191k by the focus target light flux appear to match. At this point, the focusing lens 124 is at the position where the fundus oculi Ef of the eye E, the image pick-up element 10a, etc. and the end face 152b of the optical fiber 152a are conjugate.

An examiner operates the manipulator 250 such as a joystick, moves the focus target projection optical system 191 along the light path, and matches two focus target image 191k, which are displayed on the touch panel monitor 11 or the display part 240. The focusing lens 124 moves along the light path of the imaging optical system 120 by the focus target projection optical system 191 and the cogwheel interlocking mechanism, and causes the fundus oculi Ef of the eye E, the image pick-up element 10a, etc. and the end face 152b of the optical fiber 152a to be conjugate.

With this focus adjustment, the focus is corrected in accordance with the diopter of the eye E and, as shown in FIG. 7A, the signal light LS is condensed at the fundus oculi Ef, with the reflection light and the backscattering from the fundus oculi Ef being condensed at the end face 152b of the optical fiber 152a.

When the alignment adjustment and the focus adjustment are completed, the examiner presses the start button of the manipulator 250 and causes the optical image measuring device 1 to start measurement (S05).

With a press of the start button, the controller 210 outputs the drive signal to the reference mirror drive mechanism 178a and places the reference mirror 174a in the position that corresponds to the fundus oculi Ef (S06).

Figure 7B:
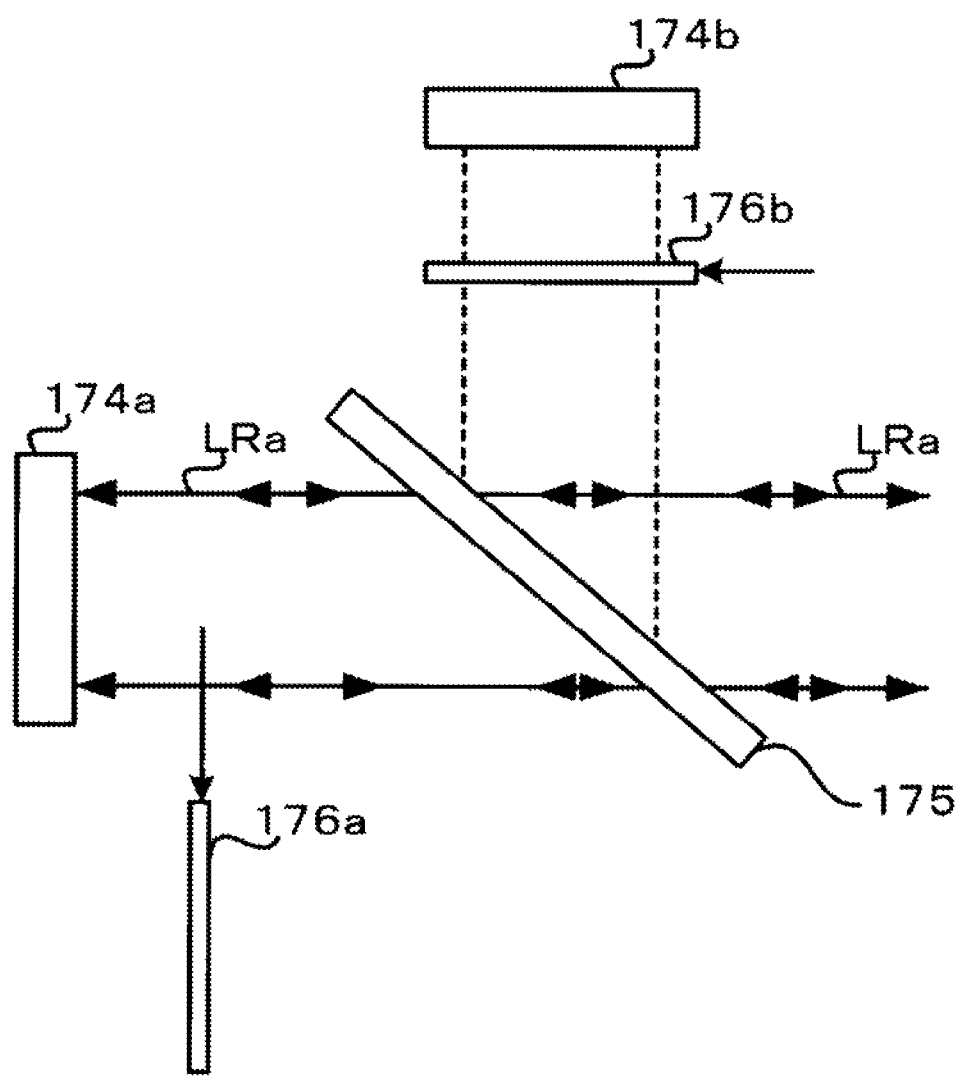
FIG. 7B is a figure showing the first aspect in the operation of the optical image measuring device according to the present embodiment.

Furthermore, the controller 210 outputs the drive signal to the light path length switch mechanism 177b and, as shown in FIG. 7B, causes the shading plate 176b to be inserted into the second light path that reaches the reference mirror 174b (S07).

With this placement of the reference mirror 174a, the optical path length of the reference light LR becomes a distance that corresponds to the optical path length that reaches the depth zone of the fundus oculi Ef. This placement position is a predetermined position and when the reference mirror 174a that is moved to this position is detected by a sensor, etc., the output of the drive signal may be terminated. Also, the drive signal is output to the light path length switch mechanism 177b that moves the shading plate 176b which shields the second light path of an optical path length that reaches the depth zone of the anterior segment Ea and by closing the second light path, the optical image measuring device 1 is in a state for obtaining OCT images of the fundus oculi Ef.

Then, the controller 210 controls the low-coherence light source 160, the scan unit 141, the CCD 184, etc. and runs a measurement of the fundus oculi Ef (S08). In addition, at the time of this measurement, the eye E is fixated by an internal fixation target, as required. The image forming part 220 collects detection signals corresponding to the fundus oculi Ef, which is output from the CCD 184 (S09) and forms tomographic images of the fundus oculi Ef based on the detection signals (S10). Formation of tomographic images uses a so-called means of Fourier domain OCT, and visualizes an aspect of the direction of depth (z-direction) of the eye E by Fourier transforming a spectrum intensity distribution of the interference light that is obtained by dividing light into spectra via diffraction grating 182.

Figure 9A:
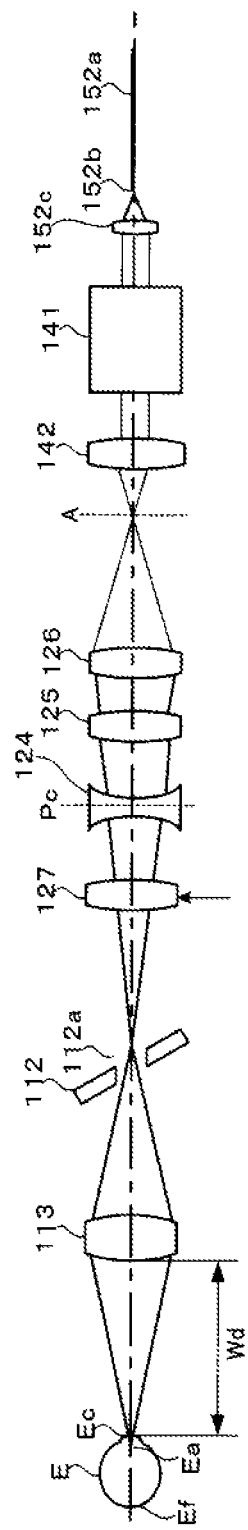
FIG. 9A is a figure showing the second aspect in the operation of the optical image measuring device according to the present embodiment.

When collection of the detection signals of the fundus oculi component is completed, the controller 210 outputs the drive signal to the lens insertion/retraction mechanism 129 and, as shown in FIG. 9A, causes the depth zone switching lens 127 to be inserted into the light path of the imaging optical system 120 (S11). Also, the controller 210 causes the focusing lens 124 to be moved to a predetermined position (S12).

With the insertion of this depth zone switching lens 127, as shown in FIG. 9A, the signal light LS is focused on the anterior segment Ea mainly involves the cornea. In other words, due to this depth zone switching lens 127 causing the anterior segment Ea and the end face 152b of the optical fiber 152a, and the anterior segment Ea and image pick-up elements 10a, 12a to be conjugate, the anterior segment Ea becomes focused. In addition, by moving the focusing lens 124 to a predetermined position, this conjugation relationship becomes stricter, and the anterior segment Ea becomes more vivid.

Figure 9B:
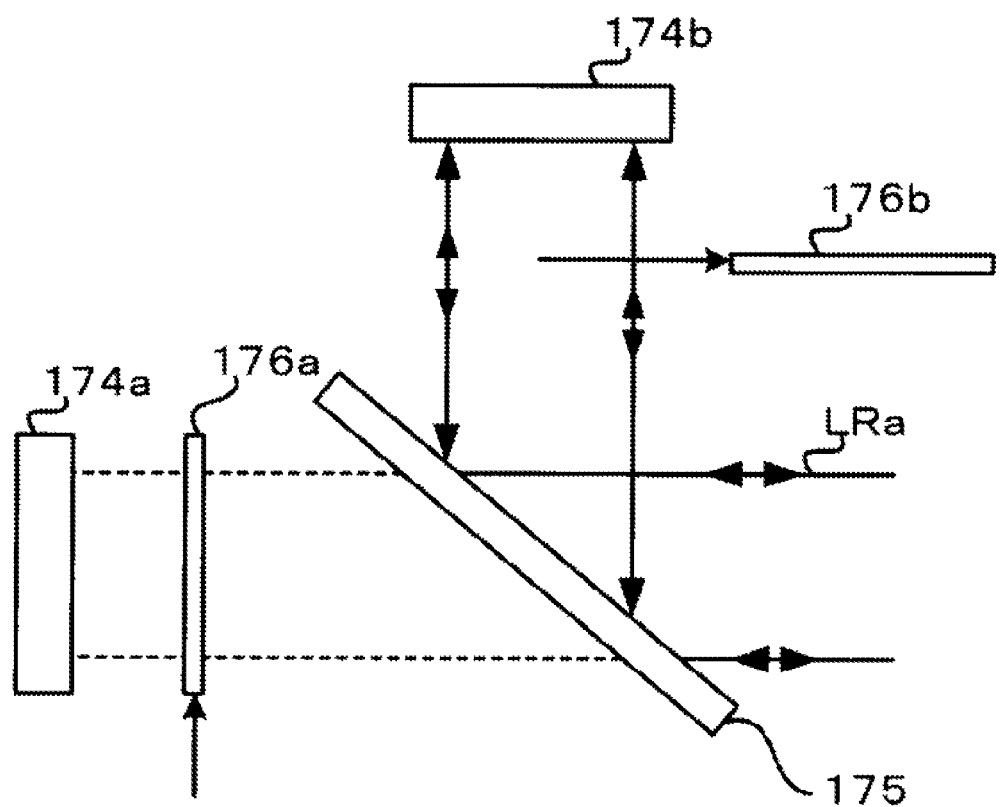
FIG. 9B is a figure showing the second aspect in the operation of the optical image measuring device according to the present embodiment.

In addition, the controller 210 outputs the drive signal to the reference mirror drive mechanism 178b and places the reference mirror 174b in a position that corresponds to the anterior segment Ea (S13). Also, the controller 210 outputs the drive signal to light path length switch mechanisms 177a and 177b and, as shown in FIG. 9B, retracts the shading plate 176b from the second light path that reaches the reference mirror 174b (S14) in addition to causing the shading plate 176a to be inserted into the first light path that reaches the reference mirror 174a (S15).

With this placement of the reference mirror 174b, the optical path length of the reference light LR becomes a distance that corresponds to the optical path length that reaches the depth zone of the anterior segment Ea.

This placement position is a predetermined position and when the reference mirror 174b that is moved to this position is detected by a sensor, etc. the output of the drive signal may be terminated. Also, by shielding the first light path that is of an optical path length that reaches the depth zone of the fundus oculi Ef with the shading plate 176a, the optical image measuring device 1 is in a state for obtaining OCT images of the anterior segment Ea.

Then, the controller 210 controls the low-coherence light source 160, the scan unit 141, the CCD 184, etc. and runs a measurement of the anterior segment Ea (S16). In addition, at the time of this measurement, the eye E is fixated by an internal fixation target as required. The image forming part 220 collects the detection signals corresponding to the anterior segment Ea that is output from the CCD 184 (S17) and forms tomographic images of the anterior segment Ea based on the detection signals (S18).

Figure 10A:
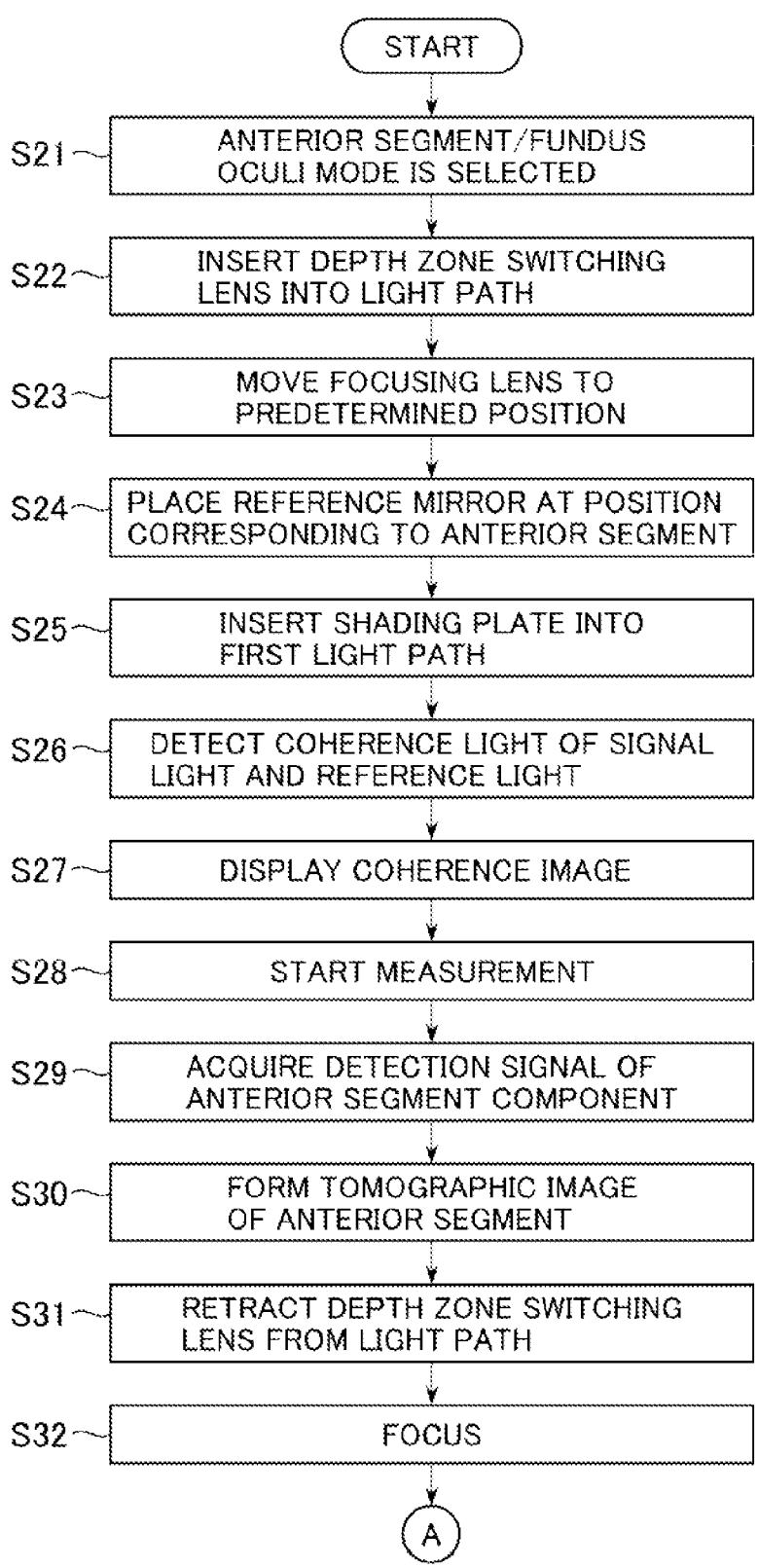
FIG. 10A is a flow chart showing the first half of the second operation of the optical image measuring device according to the present embodiment.
Figure 10B:
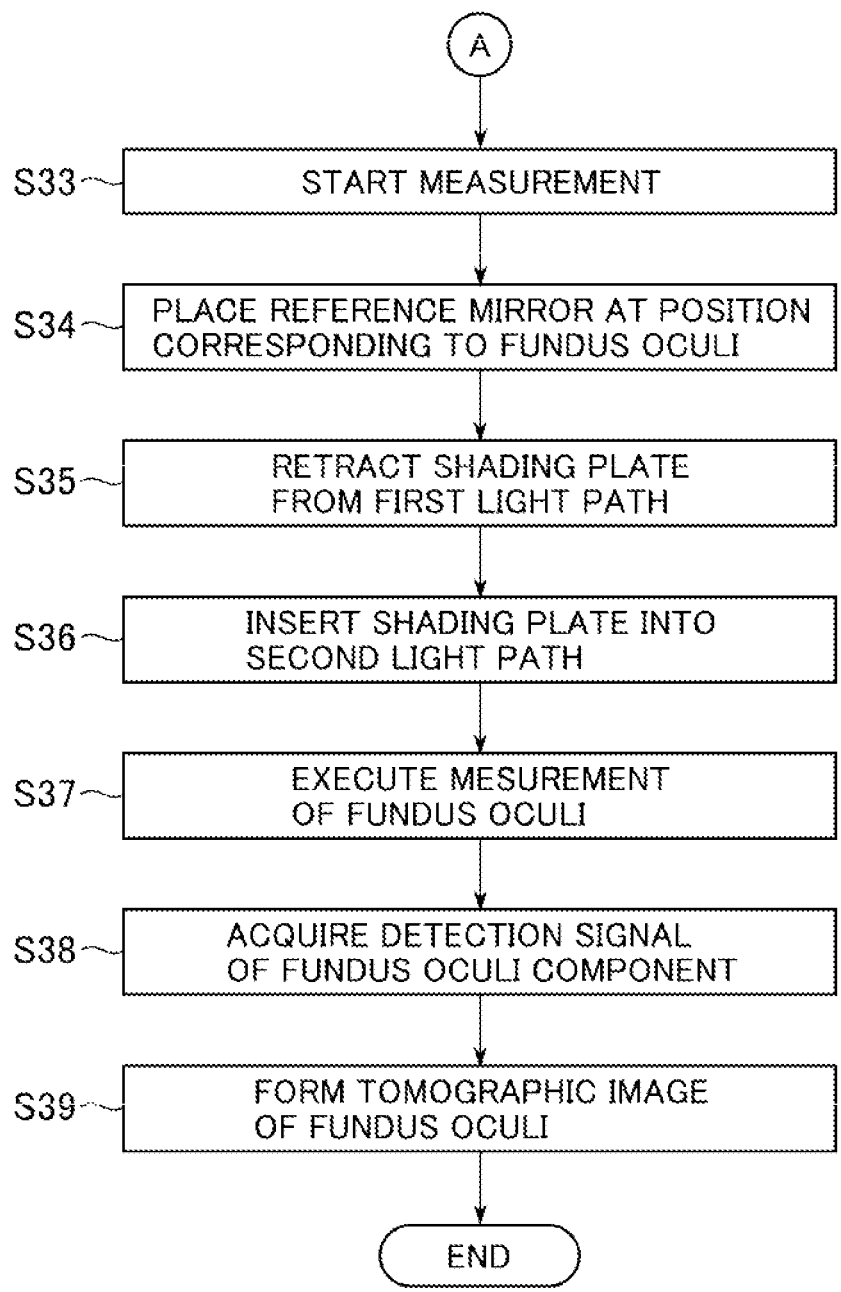
FIG. 10B is a flow chart showing the second half of the second operation of the optical image measuring device according to the present embodiment.

The flow charts shown in FIG. 10A and FIG. 10B represent an example of an operation of the optical image measuring device 1 when it is in the anterior segment fundus oculi mode that measures the fundus oculi Ef using the optical imaging measurement technology after measuring the anterior segment Ea using the optical imaging measurement technology.

At first, the controller 210 accepts a selection operation that is in the anterior segment fundus oculi mode via a press of the mode selection button that is located in the manipulator 250 (S21). With the selection of this anterior segment fundus oculi mode, the controller 210 outputs the drive signal to the lens insertion/retraction mechanism 129 and, as shown in FIG. 9A, inserts the depth zone switching lens 127 into the light path of the imaging optical system 120 (S22). Also, the controller 210 causes the focusing lens 124 to move to a predetermined position (S23).

In addition, the controller 210 outputs the drive signal to the reference mirror drive mechanism 178b and places the reference mirror 174b in a position that corresponds to the optical path length of the anterior segment Ea (S24). Also, the controller 210 outputs the drive signal to the light path length switch mechanism 177a and, as shown in FIG. 9B, causes the shading plate 176a to be inserted into the first light path that reaches the reference mirror 174a (S25).

After S21 to S25, the controller 210 controls the alignment of the optical system against the eye E. In particular, the controller 210 controls the low-coherence light source 160, the scan unit 141, the CCD 184, etc. and causes the interference light LC of the signal light LS and the reference light LR to be detected (S26). Then, the controller 210 causes an interference image that is output by the CCD 184 to be displayed on the display part 240 (S27).

Figure 11A:
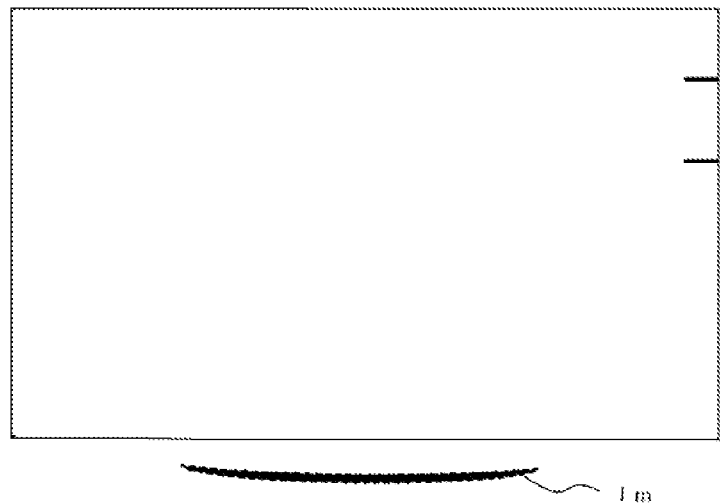
FIG. 11A is a figure showing a display aspect of working distance adjustment of the optical image measuring device according to the present embodiment.
Figure 11B:
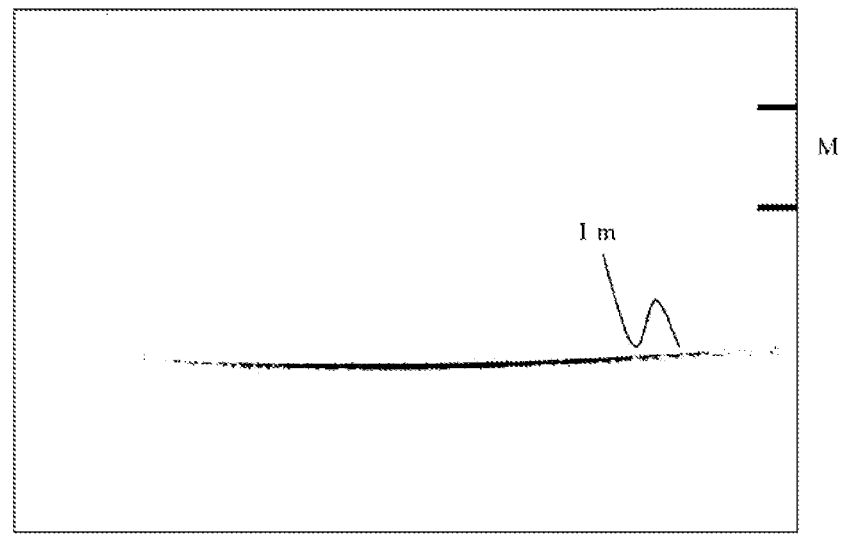
FIG. 11B is a figure showing a display aspect of working distance adjustment of the optical image measuring device according to the present embodiment.

The interference image is a result of visualization using the means of Fourier domain OCT. If the distance between the corneal vertex Ec and the objective lens 113 does not match the working distance Wd, as shown in FIG. 11A, an interference image Im that is a result of interference between the signal light LS, which are reflected by the anterior segment Ea that includes the cornea, and the reference light LR is out of the range in which the depth of the anterior segment Ea is visualized and cannot be confirmed visually by the interference image. Also, if the distance between the corneal vertex Ec and the objective lens 113 does not match the working distance Wd, as shown in FIG. 11B, the interference image Im that results from interference between the signal light LS, which are reflected from the anterior segment Ea that includes the cornea, and the reference light LR can be confirmed visually in a different position from the time when the distance matches the working distance Wd.

Figure 11C:
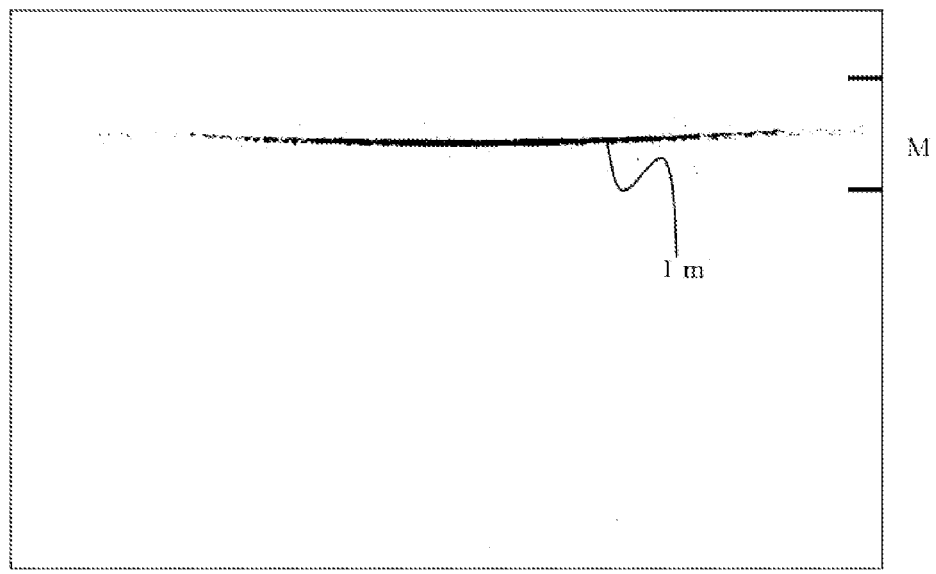
FIG. 11C is a figure showing a display aspect of working distance adjustment of the optical image measuring device according to the present embodiment.

Therefore, the examiner, as shown in FIG. 11C, adjusts the positional relationship between the eye E and the retinal camera unit 1A such that the interference image Im is displayed in a determined position of the display part 240. Within the image that is displayed by the display part 240, a maker M that indicates the determined position may be displayed. The examiner adjusts the positional relationship between the eye E and the retinal camera unit 1A such that the interference image Im overlaps this maker M.

In addition, the controller 210 may light the alignment light source 190a of the alignment optical system 190A. The examiner projects alignment bright points P1 and P2 on the eye E and while observing this state, using position adjustment of the retinal camera unit 1A, which is performed concurrently, the adjustment accuracy for matching the working distance Wd further improves.

When the alignment adjustment is completed, the examiner presses the start button of the manipulator 250, causing the optical image measuring device 1 to start measuring (S28). With this press of the start button, the controller 210 causes the detection signals corresponding to the anterior segment that is output by the CCD 184 to be collected to the image forming part 220 (S29) and causes the image forming part 220 to form tomographic images of the anterior segment Ea (S30).

When collection of the detection signals of the anterior segment component is completed, the controller 210 outputs the drive signal to the lens insertion/retraction mechanism 129, and, as shown in FIG. 7A, retracts the depth zone switching lens 127 from the light path of the imaging optical system 120 (S31). Then, the controller 210 lights the target projection light source 191b such that the focus against the eye E can be adjusted (S32).

When the focus adjustment is completed, the examiner represses the start button of the manipulator 250, causing the optical image measuring device 1 to start measuring (S33).

With a press of this start button, the controller 210 outputs the drive signal to the reference mirror drive mechanism 178a, causing the reference mirror 174a to be placed in a position that corresponds to the optical path length of the fundus oculi Ef (S34). Also, the controller 210 outputs the drive signal to light path length switch mechanisms 177a and 177b, and, as shown in FIG. 7B, retracts the shading plate 176a from the first light path that reaches the reference mirror 174a (S35) and also causes the shading plate 176b to be inserted into the second light path that reaches the reference mirror 174b (S36).

The low-coherence light source 160, the scan unit 141, the CCD 184, etc. are controlled and a measurement of the fundus oculi Ef is performed (S37). In addition, at the time of this measurement, the eye E is fixated by the internal fixation target as required. The image forming part 220 collects the detection signals corresponding to the fundus oculi that is output by the CCD 184 (S38) and forms the tomographic image of the fundus oculi Ef based on this detection signal (S39).

The actions and effects of the optical image measuring device 1 will be described.

The optical image measuring device 1 functions as follows. At first, the optical image measuring device 1 includes the imaging optical system 120 that condenses the signal light LS at the first depth zone. In addition, the optical image measuring device 1 includes the depth zone switching lens 127 that condenses the signal light LS at the second depth zone that is different from the first depth zone when the distance between the eye E and the objective lens 113 is located at the working distance Wd. The depth zone switching lens 127 can be inserted into and removed from the imaging optical system 120. Also, the optical image measuring device 1 includes the switching part that switches the light path of the reference light LR to the optical path length that corresponds to the first depth zone and the second depth zone.

Therefore, even though this optical image measuring device 1 has the imaging optical system 120 that condenses the signal light LS at the first depth zone, by inserting the depth zone switching lens 127 and switching the light path of the reference light LR to the optical path length that corresponds to the second depth zone by the switching part, the signal light LS that is reflected at the second depth zone that is different from the first depth zone can be efficiently collected. Hence, even with the optical image measuring device 1 that has the imaging optical system 120 that mainly measures a first depth zone, detailed information of each depth position of the second depth zone can be collected and the entire second depth zone can be vividly visualized.

Figure 12A:
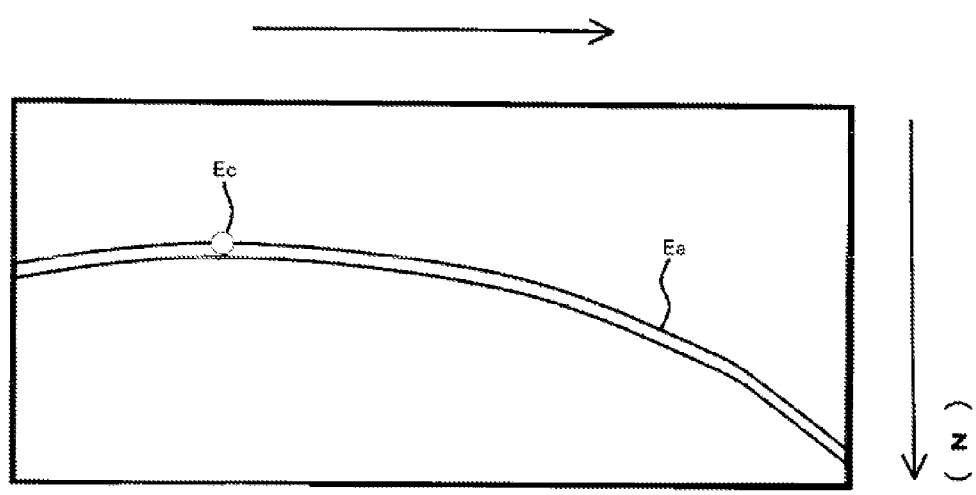
FIG. 12A is a schematic figure showing OCT images of a fundus oculi and an anterior segment formed by the optical image measuring device according to the present embodiment.
Figure 12B:
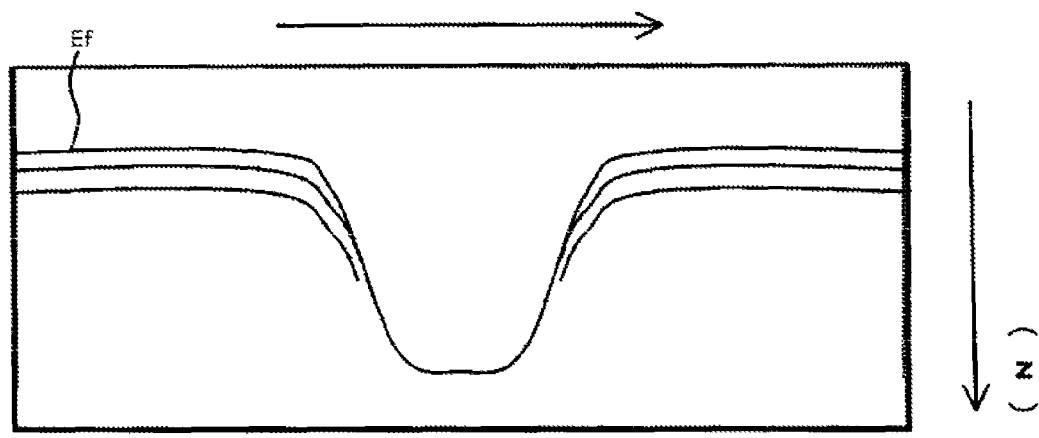
FIG. 12B is a schematic figure showing OCT images of a fundus oculi and an anterior segment formed by the optical image measuring device according to the present embodiment.
Figure 13:
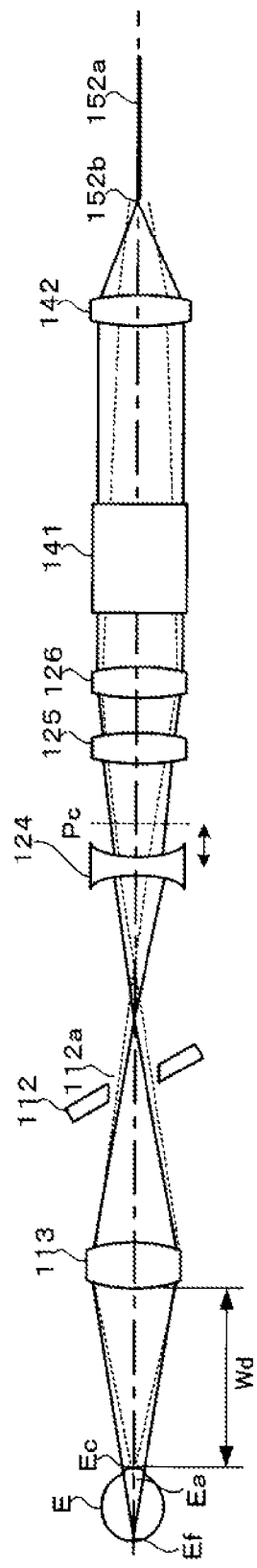
FIG. 13 is a figure for explaining focusing in the conventional optical image measuring device.
Figure 14A:
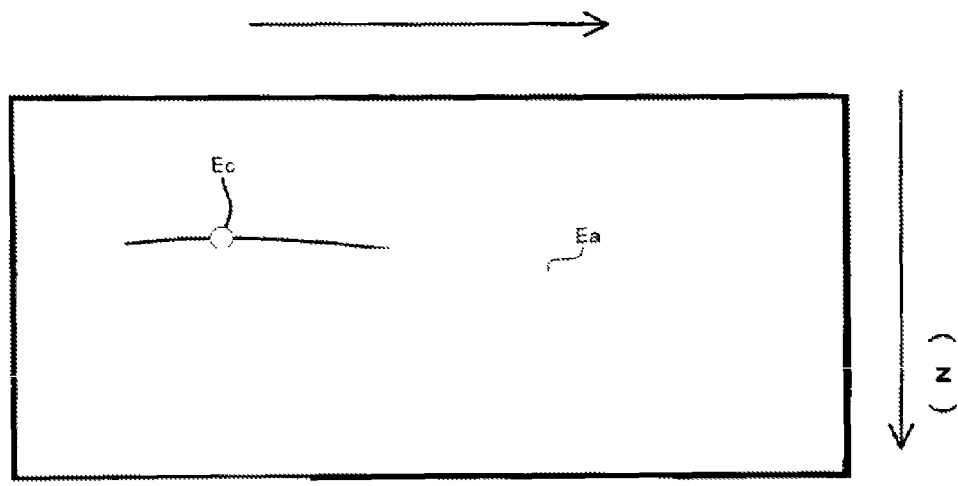
FIG. 14A is a schematic figure showing OCT images of a fundus oculi and an anterior segment formed by the conventional optical image measuring device.
Figure 14B:
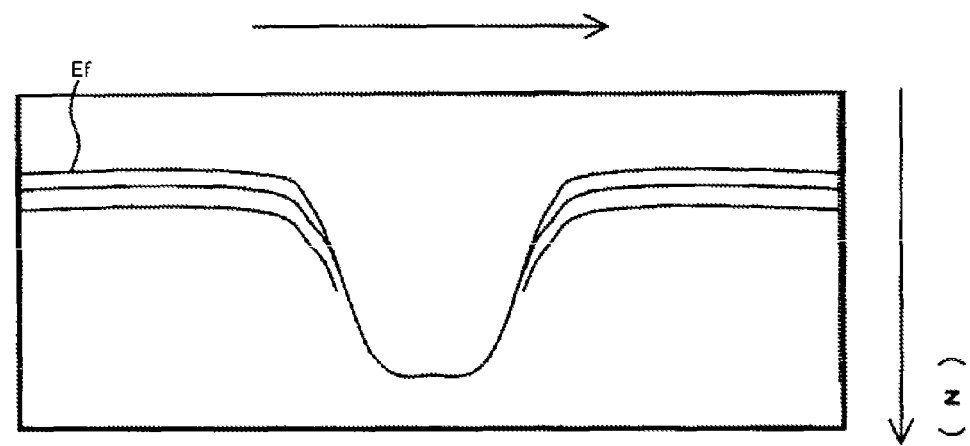
FIG. 14B is a schematic figure showing OCT images of a fundus oculi and an anterior segment formed by the conventional optical image measuring device.

For example, as described in this embodiment, when the first depth zone is considered to be the fundus oculi Ef and the second depth zone is considered to be the anterior segment Ea, this optical image measuring device 1 can obtain not only an OCT image of the fundus oculi Ef that is shown in FIG. 12B but also an OCT image of the anterior segment Ea vividly, as shown in FIG. 12A, by inserting the depth zone switching lens 127. In the OCT image of the anterior segment Ea that is obtained by this optical image measuring device 1, not only the surface of the cornea but also each tomographic position of the anterior segment Ea becomes vivid.

In addition, in this optical image measuring device 1, the controller 210 that controls it, after controlling to adjust alignments, adjust focus, and switch the light path of the reference light LR to the optical path length that corresponds to the first depth zone, causes an OCT image of the first depth zone to be obtained, then after controlling to insert the depth zone switching lens 127 to the imaging optical system 120 and to switch the light path of the reference light LR to the optical path length that corresponds to the second depth zone, causes an OCT image of the second depth zone to be obtained.

Therefore, after adjusting a first alignment and adjusting the focus, an OCT image of the first depth zone and an OCT image of the second depth zone can be obtained sequentially without being operated by the examiner, thus reducing the burden on the examiner and the subject as well as shortening the measuring time.

Also, the controller 210 that controls the optical image measuring device 1, after controlling to insert the depth zone switching lens 127 and switch the light path of the reference light LR to the optical path length that corresponds to the anterior segment Ea, outputs the low-coherence light L0 and causes the interference light LC of the reference light LR and the signal light LS to be detected.

The working distance Wd is defined generally as the distance between the corneal vertex Ec and the objective lens 113. Therefore, if the interference light LC of the signal light LS and the reference light LR, which are reflected at the anterior segment Ea, can be detected, the distance between corneal vertex Ec and the objective lens 113 is said to match the working distance Wd.

Therefore, the controller 210 of the optical image measuring device 1, after detecting this interference light LC and adjusting to the working distance Wd that is based on a display of a predetermined position of the interference image, causes an OCT image of the anterior segment Ea to be obtained, followed by, after controlling to retract the depth zone switching lens 127 from the imaging optical system 120 and switch the light path of the reference light LR to the optical path length that corresponds to the fundus oculi Ef, an OCT image of the fundus oculi Ef to be obtained.

Therefore, the accuracy in match the distance between the corneal vertex Ec and the objective lens 113 to the working distance Wd improves.

The configuration described above is merely one example for implementing the present invention. A person who intends to implement the present invention can make any modification within the scope of the present invention.

In the above embodiment, although the light path of the reference light LR is switched to the optical path length of the first depth zone and the second depth zone, this optical path length may be switched to correspond to another different depth zones. In such a case, when another depth zone switching lens 127 that condenses the signal light LS at another different depth zone is also comprised in a way that is capable of inserting and removing, and when obtaining an OCT image of another different depth zone, another depth zone switching lens 127 is inserted.

As a means of switching the optical path length of the light path of the reference light LR, not only the embodiment mentioned above but also various types of aspects can be applied. For example, only one reference mirror being placed on the light path of the reference light LR and an optical path length that corresponds to various depth zones may be realized by moving the reference mirror along the light path. When obtaining an OCT image of the first depth zone, the reference mirror is moved to a position such that the optical path length of the reference light LR corresponds to the first depth zone. When obtaining an OCT image of the second depth zone, the reference mirror is moved to a position such that the optical path length of the reference light LR corresponds to the second depth zone.

The computer program used in the above embodiment can be stored in any kind of recording medium that can be read by a drive device of a computer. As this recording medium, for example, an optical disk, a magneto-optic disk (CD-ROM, DVD-RAM, DVD-ROM, MO, and so on), and a magnetic storing medium (a hard disk, a Floppy Disk™, ZIP, and so on) can be used. Moreover, it is possible to store into a storing device such as a hard disk drive and a memory. Besides, it is possible to transmit/receive this program through a network such as the internet and a LAN.

The invention claimed is:

1. An optical image measuring device that forms tomographic images of at least a first depth zone and a second depth zone of a measured object, respectively, comprising:
    a splitting part configured to split a light from a light source into a signal light and a reference light;
    a first light path configured to be capable of adjusting an optical path length of said reference light to an optical path length that corresponds to said first depth zone;
    a second light path configured to be capable of adjusting an optical path length of said reference light to an optical path length that corresponds to said second depth zone;
    an optical system comprising an objective lens and a focusing lens, and configured to illuminate said measured object with said signal light;
    an optical system comprising an objective lens and a focusing lens, and configured to condense said signal light into said first depth zone;
    an interference light generation part configured to generate an interference light by causing interference with said signal light reflected from said first depth zone and said reference light via said first light and generate an interference light by causing interference with said signal light reflected from said second depth zone and said reference light via said second light path;
    a detecting part configured to detect each of the interference light corresponding to said first depth zone and the interference light corresponding to said second depth zone; and
    an image forming part configured to form tomographic images of said first depth zone and said second depth zone, respectively, based on the detection by said detecting part.

2. The optical image measuring device according to claim 1, wherein a part of said first light path and a part of said second light path are common.

3. The optical image measuring device according to claim 1, wherein said optical system is configured to condense said signal light into said first depth zone, further comprising:
    a switching part configured to switch an optical path length of said reference light to optical path lengths that correspond to at least said first depth zone and said second depth zone;
    a depth zone switching lens configured to be placed in a way that allows it to be inserted into and removed from said optical system, and condense said signal light into said second depth zone when it inserted into said optical system with said measured object and said objective lens positioned at a predetermined working distance; and a control part configured to insert said depth zone switching lens into said optical system when the optical path length is switched to the optical path length that corresponds to said second depth zone by said switching part; wherein:

said interference light generation part is configured to generate an interference light by causing interference with said signal light via said optical system after being reflected from said measured object and said reference light via a light path of the optical path length that has been switched by said switching part;

said detecting part is configured to detect each of said interference lights in accordance with the control by said control part; and said image forming part is configured to form tomographic images of said first depth zone and said second depth zone, respectively, based on the detection by said detecting part.

4. The optical image measuring device according to claim 3, wherein:

said measured object is a living eye;

said switching part is configured to switch to optical path lengths that correspond to a fundus oculi as said first depth zone and an anterior segment as said second depth zone;

said focusing lens is configured to be changed in the placement position depending on the diopter of said living eye when the optical path length is switched to the optical path length that corresponds to said first depth zone by said switching part; and said control part is configured to change the placement position of said focusing lens to a predetermined position when the light path of said reference light is switched by said switching part to the optical path length that corresponds to said second depth zone.

5. The optical image measuring device according to claim 3, wherein:

said measured object is the living eye;

said switching part is configured to switch to optical path lengths that correspond to a fundus oculi as said first depth zone and an anterior segment as said second depth zone;

said optical system is configured to condense said signal light into said fundus oculi;

said depth zone switching lens is configured to condense said signal light into said anterior segment when it is inserted into said optical system with said living eye and said objective lens positioned in the predetermined working distance; and said control part is configured to perform:

a first control process that causes said detecting part to detect said interference light that is generated based on the signal light that is reflected from said fundus oculi after a distance between said living eye and said objective lens is matched to said working distance;

a second control process that, after said first control process, switches the light path of said reference light to an optical path length that corresponds to a depth zone of said anterior segment and also inserts said depth zone switching lens into said optical system while maintaining said working distance; and a third control process that, after said second control process, cause said detecting part to detect said interference light that is generated based on the signal light that is reflected from said anterior segment.

6. The optical image measuring device according to claim 5, wherein:

said first control process is performed after a focus adjustment that changes the placement position of said focusing lens depending on the diopter of said living eye; and said second control process comprises a control process that changes the placement position of said focusing lens to a predetermined position.

7. The optical image measuring device according to claim 3, wherein:

said measured object is the living eye;

said switching part is configured to switch to optical path lengths that correspond to a fundus oculi as said first depth zone and an anterior segment as said second depth zone;

said optical system is configured to condense said signal light into said fundus oculi;

said depth zone switching lens is configured to condense said signal light into said anterior segment when it is inserted into said optical system with said living eye and said objective lens positioned in the predetermined working distance; and said control part is configured to perform:

a first control process that switches the light path of said reference light to the optical path length that corresponds to said anterior segment and also inserts said depth zone switching lens into said optical system;

a second control process that, after the first control process, causes said detecting part to output a detection result of said interference light based on the signal light that is reflected from said anterior segment;

a third control process that, after matching a distance between said living eye and said objective lens that corresponds to said detection result from said second control process to said working distance, switches the optical path length to the optical path length that corresponds to a depth zone of said fundus oculi and also retracts said depth zone switching lens from said optical system while maintaining said working distance; and a fourth control process that, after the third control process, causes said detecting part to detect said interference light that is generated based on the signal light that is reflected from said fundus oculi.

8. The optical image measuring device according to claims 3 through 7, said switching part comprising:

a beam splitter that split a reference light that is split from the light from said light source into two;

a first light path through which one of said two reference lights goes and that has an optical path length that corresponds to said first depth zone;

a second light path through which the other one of said two reference lights and that has an optical path length that corresponds to said second depth zone; and a shading plate that shields said first and second light paths selectively, wherein said control part is configured to insert said depth zone switching lens in synchronization with insertion of said shading plate into said first light path.

9. A control method of the optical image measuring device, having a splitting part that splits a light from a light source into a signal light and a reference light, an optical system that comprises an objective lens and a focusing lens and that condenses said signal light to a fundus oculi, an interference light generation part that generates an interference light by causing interference with said signal light via said optical system after being reflected from said living eye and said reference light via a light path of the predefined optical path length, and a detecting part that detects said interference light, and forming a tomographic image based on a detection signal that is output from said detecting part, and the method comprising:

a first control process that matches the distance between said living eye and the objective lens to said working distance;

a second control process that switches the optical path length of said reference light to a first optical path length that corresponds to the depth zone of said fundus oculi;

a third control process that, after said first and second control processes, causes said detecting part to detect the interference light of the signal light reflected from said fundus oculi and said reference light via the light path of said first optical path length;

a fourth control process that, after said third control process, switches the optical path length of said reference light to a second optical path length that corresponds to a depth zone of the anterior segment of said living eye;

a fifth control process that, in synchronization with the fourth control process, inserts a depth zone switching lens that condenses said signal light to said anterior segment to said optical system while keeping said living eye and said objective lens positioned at said predetermined working distance;

a sixth control process that, after said fourth and fifth processes, causes said detecting part to detect the interference light of said signal light reflected from said anterior segment and the reference light via a light path of said second optical path length; and a seventh control process that forms tomographic images of said fundus oculi and anterior segment based on interference lights detected in said third process and said sixth process, respectively.

10. The control method of optical image measuring device according to claim 9, wherein;

said first control process comprises a control process that changes the placement position of said focusing lens depending on the diopter of said living eye; and the method further comprising an eighth control process that, in synchronization with said fourth control process and said fifth control process, moves said focusing lens to a predetermined placement position.

11. A control method of the optical image measuring device, having a splitting part that splits a light from a light source into a signal light and a reference light, an optical system that comprises an objective lens and a focusing lens and that condenses said signal light to a fundus oculi, an interference light generation part that generates an interference light by causing interference with said signal light via said optical system after being reflected from said living eye and said reference light via a light path of the predefined optical path length, and a detecting part that detects said interference light, and forming a tomographic image based on a detection signal that is output from said detecting part, and the method comprising:

a first control process that switches the optical path length of said reference light to a first optical path length that corresponds to the depth zone of an anterior segment of said living eye and also inserts the depth zone switching lens that condenses said signal light to said anterior segment to said optical system;

a second control process that causes said detecting part to detect an interference light of said signal light reflected from said anterior segment and the reference light via the light path of said first optical path length;

a third control process that matches a distance between said living eye and objective lens to a predetermined working distance based on a detection result of said interference light;

a fourth control process that, after said third control process, switches the optical path length of said reference light to a second optical path length that corresponds to the depth zone of said fundus oculi;

a fifth control process that, in synchronization with said fourth control process, retracts said depth zone switching lens from said optical system;

a sixth control process that, after said third and fourth control processes, causes said detecting part to detect an interference light of said signal light reflected from the fundus oculi and said reference light via the light path of said second optical path length; and a seventh control process that forms a tomographic image of said fundus oculi based on the interference light detected in said sixth control process.

* * * * *